(12) United States Patent
Boenitz-Dulat et al.

(10) Patent No.: US 7,732,179 B2
(45) Date of Patent: *Jun. 8, 2010

(54) MUTANTS OF PYRROLOQUINOLINE QUINONE DEPENDENT SOLUBLE GLUCOSE DEHYDROGENASE

(75) Inventors: Mara Boenitz-Dulat, Tutzing (DE); Daniela Beck, Penzberg (DE); Peter Kratzsch, Penzberg (DE); Rainer Schmuck, Benediktbeuern (DE); Herbert Von Der Eltz, Weilheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/250,241

(22) Filed: Oct. 13, 2008

(65) Prior Publication Data

US 2009/0148874 A1 Jun. 11, 2009

(30) Foreign Application Priority Data

Apr. 13, 2006 (EP) .................................. 06007779
Apr. 11, 2007 (WO) ................ PCT/EP2007/003207

(51) Int. Cl.
| C12N 9/04 | (2006.01) |
| C12N 15/00 | (2006.01) |
| C12N 1/20 | (2006.01) |
| C12Q 1/32 | (2006.01) |
| C12Q 1/00 | (2006.01) |
| C12P 21/04 | (2006.01) |
| C07H 21/04 | (2006.01) |
| C12Q 1/68 | (2006.01) |

(52) U.S. Cl. ............................ 435/190; 435/440; 435/4; 435/6; 435/69.1; 435/71.1; 435/26; 435/252.3; 435/320.1; 536/23.2

(58) Field of Classification Search ....................... None
See application file for complete search history.

(56) References Cited

FOREIGN PATENT DOCUMENTS

| WO | 02/34919 | 5/2002 |
| WO | 2006/008132 | 1/2006 |

OTHER PUBLICATIONS

Branden et al. Introduction to Protein Structure, Garland Publishing Inc., New York, p. 247, 1991.*
"Molecular Engineering of PQQGDH and its Applications," S. Igarashi et al., Archives of Biochemistry and Biophysics, vol. 428, No. 1, Aug. 1, 2004, pp. 52-63.

* cited by examiner

*Primary Examiner*—Yong D Pak
(74) *Attorney, Agent, or Firm*—Barnes & Thornburg LLP

(57) ABSTRACT

A mutant of PQQ-dependent soluble glucose dehydrogenase (s-GDH; EC 1.1.5.2) is provided with improved specificity for glucose as compared to maltose, having a substitution of threonine at position 348 by either glycine, alamine or serine, wherein said mutant additionally comprises, at least one mutation for improving the stability of the mutant and one or more mutation(s) for improving the affinity of the mutant to glucose, and/or one or more mutation(s) for further improving the specificity of the mutant for glucose as compared to maltose, and wherein position 348 correspond to the amino acid positions known from the *A. calcoaceticus* s-GDH wild-type sequence. Also disclosed are genes encoding such mutant s-GDH, and different applications of these s-GDH mutants, particularly for determining the concentration of glucose in a sample.

15 Claims, 4 Drawing Sheets

Fig. 1

Amino acid sequences of A. calcoaceticus (top) and
        A. baumannii (bottom)

```
  1 DVPLTPEQFAKAKSENFDKKVILSNLNKPHALLWGPDNQIWLTERATGKI  50
    |:|||.||||||.|||||||||||||||||||||||||||||||||||||
  1 DIPLTPAQFAKAKTENFDKKVILSNLNKPHALLWGPDNQIWLTERATGKI  50

51 LRVNPESGSVKTVFQVPEIVNDADGQNGLLGFAFHPDFKNNPYIYISGTF 100
    ||||  ||| ||||||||||||.|||||||||||||||||.||||||||
 51 LRVNPVSGSAKTVFQVPEIVSDADGQNGLLGFAFHPDFKHNPYIYISGTF 100

101 KNPKSTDKELPNQTIIRRYTYNKSTDTLEKPVDLLAGLPSSKDHQSGRLV 150
    ||||||||||||||||||||||.||| |||:||:||:|||||||||||||
101 KNPKSTDKELPNQTIIRRYTYNKTTDTFEKPIDLIAGLPSSKDHQSGRLV 150

151 IGPDQKIYYTIGDQGRNQLAYLFLPNQAQHTPTQQELNGKDYHTYMGKVL 200
    |||||||||||.||||||||||||.|||||||||||||.|||||||||| 
151 IGPDQKIYYTICDQGRNQLAYLFLSNQAQHTPTQQELNSKDYHTYMGKVL 200

201 RLNLDGSIPKDNFSFNGVVSHIYTLGHRNPQGLAFTPNGKLLQSEQGPNS 250
    |||||||||||||||||||||||||||||||||| |||||||||||||||
201 RLNLDGSIPKDNPSFNGVVSHIYTLGHRNPQGLAFAPNGKLLQSEQGPNS 250

251 DDEINLIVKGGNYGWPNVAGYKDDSGYAYANYSAAANKS.IKDLAQNGVK 299
    ||||||:.||||||||||||||||||||||||||||| ||| ||||||:|
251 DDEINLVLKGGNYGWPNVAGYKDDSGYAYANYSAATNKSQIKDLAQNGIK 300

300 VAAGVPVTKESEWTGKNFVPPLKTLYTVQDTYNYNDPTCGEMTYICWPTV 349
    || |||||||||||||||||||||||||||||||||||||||| ||||||
301 VATGVPVTKESEWTGKNFVPPLKTLYTVQDTYNYNDPTCGEMAYICWPTV 350

350 APSSAYVYKGGKKAITGWENTLLVPSLKRGVIFRIKLDPTYSTTYDDAVP 399
    |||||||| ||||||| ||||||||||||||||||||||||||||:|| 
351 APSSAYVYTGGKKAIPGWENTLLVPSLKRGVIFRIKLDPTYSTTLDDAIP 400

400 MFKSNNRYRDVIASPDGNVLYVLTDTAGNVQKDDGSVTNTLENPGSLIKF 449
    |||||||||||||||:||||||||||||||||||||||.|||||||||||
401 MFKSNNRYRDVIASPEGNTLYVLTDTAGNVQKDDGSVTHTLENPGSLIKF 450

450 TYKAK 454
    || :
451 TYNGK 455
```

Fig. 3a

Sequence vector pACSGDH

```
cactaactga ttacgcaccg catgtaaccg ttttcaatct gtgagtaaat tcacagttta   60
ttaacattgt gatagctatg atgacaacgt tgtcgcact gtaactaacg tgtaacagtt  120
agttgtcagt tttgctgggg tatttcgctt ataaaaccg ttatcacaat atcccgcgac  180
taccggacaa aaataaagag ttgaataaga gcttatccca ttagggctat tttacttgcc  240
attttggacc tggcagtgc tcgccaaaac gcgttagcgt tttgaacgcg ctagcggcgg  300
ccgaagggc gagcgtagcg agtcaaacct cacgtactac gtgtacgctc cggttttgc   360
gcgctgtccg tgtccaaact gctgcgccaa taacgctgg tgggataggc tctaaatacg  420
cttcggcgtt cagtaacacg cgttaacgtg ctgaacagcc gggcattttt ttacgctata  480
ccctacataa taaaaccgga gctaccatga ataagaaggt actgacccctt tctgccgtga  540
tggcaagtct gttattcggc gcgcacgcgc atgcgccga tgttcctcta actccatctc  600
aatttgctaa agcgaaatca gagaactttg acaagaaagt tattctatct aatctaaata  660
agccgcacgc gttgttatgg ggaccagata atcaaatttg gttaactgag cgagcaacag  720
gtaagattct aagagtaat ccagagtcgg gtagtgtaaa aacagttttt caggtaccag  780
agattgtcaa tgatgctgat gggcagaatg gtttattagg ttttgccttc catcctgatt  840
ttaaaaataa tccttatatc tatatttcag gtacatttaa aaatccgaaa tctacagata  900
aagaattacc gaaccaaacg attattcgtc gttaaccta taataaatca acagatacgc  960
tcgagaagcc agtcgattta ttagcaggat taccttcatc aaaagaccat cagtcaggtc 1020
gtcttgtcat tgggccagat caaaagattt attatacgat tggtgaccaa gggcgtaacc 1080
agcttgctta tttgttcttg ccaaatcaag cacaacatac gccaactcaa caagaactga 1140
atggtaaaga ctatcacacc tatatgggta aagtactacg cttaaatctt gatggaagta 1200
ttccaaagga taatccaagt tttaacgggg tggttagcca tatttataca cttggacatc 1260
gtaatccgca gggcttagca ttcactccaa atggtaaatt attgcagtct gaacaaggcc 1320
caaactctga cgatgaaatt aacctcattg tcaaggtgg caattatggt tggccgaatg 1380
tagcaggtta taaagatgat agtggctatg cttatgcaaa ttattcagca gcagccaata 1440
agtcaattaa ggatttagct caaatggag taaaagtagc cgcaggggtc cctgtgacga 1500
aagaatctga atggactggt aaaaactttg tcccaccatt aaaaacttta tataccgttc 1560
aagataccta caactataac gatccaactt gtggagagat gacctacatt gctggccaa  1620
cagttgcacc gtcatctgcc tatgtctata agggcggtaa aaaagcaatt actggttggg 1680
aaaatacatt attggttcca tctttaaaac gtggtgtcat tttccgtatt aagttagatc 1740
caacttatag cactacttat gatgacgctg taccgatgtt taagagcaac aaccgttatc 1800
gtgatgtgat tgcaagtcca gatgggaatg tcttatatgt attaactgat actgccgaa  1860
atgtccaaaa agatgatggc tcagtaacaa atacattaga aaaccagga tctctcatta 1920
agttcaccta taaggctaag taatacagtc gcattaaaaa accgatctat aaagatcggt 1980
ttttttagtt ttagaaaaga attcactggc cgtcgtttta caacgtcgtg actgggaaaa 2040
ccctggcgtt acccaactta atcgccttgc agcacatccc ccttcgcca gctggcgtaa 2100
tagcgaagag gcccgcaccg atcgccctt caacagttg cgcagcctga atggcgaatg 2160
gcgcctgatg cggtatttc tccttacgca tctgtgcggt atttcacacc gcatatggtg 2220
cactctcagt acaatctgct ctgatgccgc atagttaagc agcccgac accgccaac   2280
accgctgac gcgcctgac gggcttgtct gctcccggca tccgttaca gacaagctgt 2340
gaccgtctc gggagctgca tgtgtcagag gttttcaccg tcatcaccga aacgcgcgag 2400
acgaagggc ctgtgatac gcctattttt ataggttaat gtcatgataa taatggtttc 2460
ttagacgtca ggtggcactt ttcggggaaa tgtgcgcgga acccctattt gtttattttt 2520
ctaaatacat tcaaatatgt atccgctcat gagacaataa ccctgataaa tgcttcaata 2580
atattgaaaa aggaagagta tgagtattca acatttccgt gtcgccctta ttcccttttt 2640
tgcggcattt tgccttcctg ttttgctcac ccagaaacg ctggtgaaag taaaagatgc 2700
tgaagatcag ttgggtgcac gagtgggtta catcgaactg gatctcaaca gggtaagat 2760
ccttgagagt tttcgcccg aagaacgttt tccaatgatg agcacttta agttctgct  2820
atgtggcgcg gtattatccc gtattgacgc cgggcaagag caactcggtc gccgcataca 2880
```

Fig. 3b

```
ctattctcag aatgacttgg ttgagtactc accagtcaca gaaaagcatc ttacggatgg 2940
catgacagta agagaattat gcagtgctgc cataaccatg agtgataaca ctgcggccaa 3000
cttacttctg acaacgatcg gaggaccgaa ggagctaacc gcttttttgc acaacatggg 3060
ggatcatgta actcgccttg atcgttggga accggagctg aatgaagcca taccaaacga 3120
cgagcgtgac accacgatgc ctgtagcaat ggcaacaacg ttgcgcaaac tattaactgg 3180
cgaactactt actctagctt cccggcaaca attaatagac tggatggagg cggataaagt 3240
tgcaggacca cttctgcgct cggccttcc ggctggctgg tttattgctg ataaatctgg 3300
agccggtgag cgtgggtctc gcgtatcat tgcagcactg gggccagatg gtaagccctc 3360
ccgtatcgta gttatctaca cgacggggag tcaggcaact atggatgaac gaaatagaca 3420
gatcgctgag ataggtgcct cactgattaa gcattggtaa ctgtcagacc aagtttactc 3480
atatatactt tagattgatt taaaacttca ttttaattt aaaaggatct aggtgaagat 3540
cctttttgat aatctcatga ccaaaatccc ttaacgtgag ttttcgttcc actgagcgtc 3600
agaccccgta gaaaagatca aaggatcttc ttgagatcct ttttttctgc gcgtaatctg 3660
ctgcttgcaa acaaaaaaac caccgctacc agcggtggtt tgtttgccgg atcaagagct 3720
accaactctt tttccgaagg taactggctt cagcagagcg cagataccaa atactgtcct 3780
tctagtgtag ccgtagttag gccaccactt caagaactct gtagcaccgc ctacatacct 3840
cgctctgcta atcctgttac cagtggctgc tgccagtggc gataagtcgt gtcttaccgg 3900
gttggactca agacgatagt taccggataa ggcgcagcgg tcgggctgaa cggggggttc 3960
gtgcacacag cccagcttgg agcgaacgac ctacaccgaa ctgagatacc tacagcgtga 4020
gctatgagaa agcgccacgc ttcccgaagg gagaaaggcg gacaggtatc cggtaagcgg 4080
cagggtcgga acaggagagc gcacgaggga gcttccaggg ggaaacgcct ggtatcttta 4140
tagtcctgtc gggtttcgcc acctctgact tgagcgtcga ttttgtgat gctcgtcagg 4200
gggcggagc ctatgaaaa acgccagcaa cgcggccttt ttacggttcc tggccttttg 4260
ctggcctttt gctcacatgt tctttcctgc gttatcccct gattctgtgg ataaccgtat 4320
taccgccttt gagtgagctg ataccgctcg ccgcagccga acgacggggc ccg       4373
```

MUTANTS OF PYRROLOQUINOLINE QUINONE DEPENDENT SOLUBLE GLUCOSE DEHYDROGENASE

CLAIM OF PRIORITY

The present application is based on and claims priority to International Patent Application No. PCT/EP2007/003207, filed Nov. 4, 2007, which in turn is based on and claims priority to European Patent Application No. 06007779.9, filed Apr. 13, 2006, both of which are hereby incorporated by reference in their entireties.

TECHNICAL FIELD OF THE INVENTION

The present invention relates to a mutant of PQQ-dependent soluble glucose dehydrogenase (s-GDH; EC 1.1.5.2) with improved specificity for glucose as compared to maltose, having a substitution of threonine at position 348 by either glycine, alanine or serine and wherein said mutant additionally comprises, at least one mutation for improving the stability of the mutant and one or more mutation(s) for improving the affinity of the mutant to hexoses, e.g. preferably glucose, and/or one or more mutation(s) for further improving the specificity of the mutant for glucose as compared to maltose, and wherein these positions correspond to the amino acid positions known from the *A. calcoaceticus* s-GDH wild-type sequence. Also disclosed are genes encoding such mutant s-GDH, and different applications of these s-GDH mutants, particularly for determining the concentration of glucose in a sample.

BACKGROUND

The determination of blood glucose concentration is extremely important in clinical diagnosis and in the management of diabetes. Approximately 150 million people worldwide suffer from the chronic disease diabetes mellitus, a figure that may double by 2025 according to the WHO. Although diabetes is readily diagnosed and treated, successful long-term management requires low-cost diagnostic tools that rapidly and accurately report blood glucose concentrations. PQQ-dependent glucose dehydrogenases (EC 1.1.5.2) catalyze a reaction in which glucose is oxidized to gluconolactone. Consequently, this type of enzyme is used in measuring blood sugar. One of these tools is a diagnostic strip based on the soluble glucose dehydrogenase (s-GlucDOR, EC 1.1.5.2), a pyrroloquinoline quinone-containing enzyme originally derived from *Acinetobacter calcoaceticus*.

Quinoproteins use quinone as cofactor to oxidize alcohols, amines and aldoses to their corresponding lactones, aldehydes and aldolic acids (Duine, J. A., Energy generation and the glucose dehydrogenase pathway in *Acinetobacter*, in "The Biology of *Acinetobacter*" New York, Plenum Press (1991), pp. 295-312; Duine, J. A., Eur. J. Biochem. 200 (1991) 271-284; Davidson, V. L., in "Principles and applications of quinoproteins", the whole book, New York, Marcel Dekker (1993); Anthony, C., Biochem. J. 320 (1996) 697-711; Anthony, C. and Ghosh, M., Current Science 72 (1997) 716-727; Anthony, C., Biochem. Soc. Trans. 26 (1998) 413-417; Anthony, C. and Ghosh, M., Prog. Biophys. Mol. Biol. 69 (1998) 1-22. Among quinoproteins, those containing the noncovalently bound cofactor 2,7,9-tricarboxy-1H-pyrrolo[2,3-f]quinoline-4,5-dione (PQQ) constitute the largest sub-group (Duine 1991, supra). All bacterial quinone glucose dehydrogenases known so far belong to this sub-group with PQQ as cofactor (Anthony and Ghosh 1997 supra; Goodwin, P. M. and Anthony, C., Adv. Microbiol. Physiol. 40 (1998) 1-80; Anthony, C., Adv. in Phot. and Resp. 15 (2004) 203-225).

Two types of PQQ-dependent glucose dehydrogenase (EC 1.1.5.2) have been characterized in bacteria: One is membrane-bound (m-GDH); the other is soluble (s-GDH). Both types do not share any significant sequence homology (Cleton-Jansen, A. M., et al., Mol. Gen. Genet. 217 (1989) 430-436; Cleton-Jansen, A. M., et al., Antonie Van Leeuwenhoek 56 (1989) 73-79; Oubrie, A., et al., Proc. Natl. Acad. Sci. U.S.A. 96 (1999) 11787-11791. They are also different regarding both their kinetic as well as their immunological properties (Matsushita, K., et al., Bioscience Biotechnol. & Biochem. 59 (1995) 1548-1555). The m-GDHs are widespread in Gram-negative bacteria, s-GDHs, however, have been found only in the periplasmatic space of *Acinetobacter* strains, like *A. calcoaceticus* (Duine, J. A., 1991a; Cleton-Jansen, A. M. et al., J. Bacteriol. 170 (1988) 2121-2125; Matsushita and Adachi, 1993) and *A. baumannii* (JP 11243949).

Through searching sequence databases, two sequences homologous to the full-length *A. calcoaceticus* s-GDH have been identified in *E. coli* K-12 and *Synechocystis* sp. Additionally, two incomplete sequences homologous to *A. calcoaceticus* s-GDH were also found in the genome of *P. aeruginosa* and *Bordetella pertussis* (Oubrie et al. 1999 a, b, c) and *Enterobacter intermedium* (Kim, C. H. et al., Current Microbiol. 47 (2003) 457-461), respectively. The deduced amino acid sequences of these four uncharacterized proteins are closely related to *A. calcoaceticus* s-GDH with many residues in the putative active site absolutely conserved. These homologous proteins are likely to have a similar structure and to catalyze similar PQQ-dependent reactions (Oubrie et al., 1999 a, b, c; Oubrie A., Biochim. Biophys. Acta 1647 (2003) 143-151; Reddy, S., and Bruice, T. C., J. Am. Chem. Soc. 126 (2004) 2431-2438; Yamada, M. et al., Biochim. Biophys. Acta 1647 (2003) 185-192).

Bacterial s-GDHs and m-GDHs have been found to possess quite different sequences and different substrate specificity. For example, *A. calcoaceticus* contains two different PQQ-dependent glucose dehydrogenases, one designated m-GDH which is active in vivo, and the other designated s-GDH for which only in vitro activity can be shown. Cleton-Jansen et al., 1988; 1989 a, b cloned the genes coding for the two GDH enzymes and determined the DNA sequences of both of these GDH genes. There is no obvious homology between m-GDH and s-GDH corroborating the fact that m-GDH and s-GDH represent two completely different molecules (Laurinavicius, V., et al., Biologija (2003) 31-34).

The gene of s-GDH from *A. calcoaceticus* has been cloned in *E. coli*. After being produced in the cell, the s-GDH is translocated through the cytoplasmic membrane into the periplasmic space (Duine, J. A., Energy generation and the glucose dehydrogenase pathway in *Acinetobacter*, in "The Biology of *Acinetobacter*", New York, Plenum Press (1991), pp. 295-312; Matsushita, K. and Adachi, O., Bacterial quinoproteins glucose dehydrogenase and alcohol dehydrogenase, in "Principles and applications of Quinoproteins", New York, Marcel Dekker (1993) pp. 47-63). Like the native s-GDH from *A. calcoaceticus*, recombinant s-GDH expressed in *E. coli* is a homodimer, with one PQQ molecule and three calcium ions per monomer (Dokter, P. et al., Biochem. J. 239 (1986) 163-167; Dokter, P. et al., FEMS Microbiol. Lett. 43 (1987) 195-200; Dokter, P. et al., Biochem. J. 254 (1988) 131-138; Olsthoorn, A. J. and Duine, J. A., Arch. Biochem. Biophys. 336 (1996) 42-48; Oubrie, A., et al., J. Mol. Biol. 289 (1999) 319-333; Oubrie, A., et al., Proc. Natl. Acad. Sci.

U.S.A 96 (1999) 11787-11791; Oubrie, A., et al., Embo J. 18 (1999) 5187-5194). s-GDH oxidizes a wide range of mono- and disaccharides to the corresponding ketones which further hydrolyze to the aldonic acids, and it is also able to donate electrons to PMS (phenazine metosulfate), DCPIP (2,6-dichlorophenolindophenol), WB (Wurster's blue) and short-chain ubiquinones such as ubiquinone Q1 and ubiquinone Q2 (Matsushita, K., et al., Biochem. 28 (1989) 6276-6280; Matsushita, K., et al., Antonie Van Leeuwenhoek 56 (1989) 63-72), several artificial electron acceptors such as N-methylphenazonium methyl sulfate (Olsthoom, A. J. and Duine, J. A., Arch. Biochem. Biophys. 336 (1996) 42-48; Olsthoorn, A. J. and Duine, J. A., Biochem. 37 (1998) 13854-13861) and electro conducting polymers (Ye, L., et al., Anal. Chem. 65 (1993) 238-241). In view of s-GDH's high specific activity towards glucose (Olsthoom, A. J. and Duine, J. A., (1996) supra) and its broad artificial electron acceptor specificity, the enzyme is well suited for analytical applications, particularly for being used in (bio-)sensor or test strips for glucose determination in diagnostic applications (Kaufmann, N. et al., Development and evaluation of a new system for determining glucose from fresh capillary blood and heparinized blood in "Glucotrend" (1997) 1-16, Boehringer Mannheim GmbH; Woosuck, S. et al., Sensors and Actuators B 100 (2004) 395-402).

Glucose oxidation can be catalyzed by at least three quite distinct groups of enzymes, i.e., by NAD/P-dependent glucose dehydrogenases, by flavoprotein glucose oxidases or by quinoprotein GDHs (Duine, J. A., Biosens. Bioelectronics 10 (1995) 17-23). A rather slow autooxidation of reduced s-GDH has been observed, demonstrating that oxygen is a very poor electron acceptor for s-GDH (Olsthoom and Duine, 1996). s-GDH can efficiently donate electrons from the reduced quinone to mediators such as PMS, DCPIP, WB and short-chain ubiquinones such as Q1 and Q2, but it can not efficiently donate electrons directly to oxygen.

Traditional test strips and sensors for monitoring glucose level in blood, serum and urine e.g. from diabetic patients use glucose oxidase. The performance of the enzyme is dependent of the oxygen concentration. Glucose measurements at different altitudes with different oxygen concentrations in the air may lead to false results. The major advantage of PQQ-dependent glucose dehydrogenases is their independence from oxygen. This important feature is e.g., discussed in U.S. Pat. No. 6,103,509, in which some features of membrane-bound GDH have been investigated.

An important contribution to the field has been the use of s-GDH together with appropriate mediators. Assay methods and test strip devices based on s-GDH are disclosed in detail in U.S. Pat. No. 5,484,708. This patent also contains detailed information on the set-up of assays and the production of s-GDH-based test strips for measurement of glucose. The methods described there as well as in the cited documents are herewith included by reference.

Other patents or applications relating to the field and comprising specific information on various modes of applications for enzymes with glucose dehydrogenase activity are U.S. Pat. No. 5,997,817; U.S. Pat. No. 6,057,120; EP 0 620 283; and JP 11-243949-A.

A commercial system which utilizes s-GDH and an indicator that produces a color change when the reaction occurs (Kaufmann, et al., 1997, supra) is the Glucotrend® system distributed by Roche Diagnostics GmbH.

Despite the above discussed advantages for use of a PQQ dependent s-GDH, in the determination of glucose also a disadvantage has to be considered. The enzyme has rather a broad substrate spectrum as compared to m-GDH. That is, s-GDH oxidizes not only glucose but also several other sugars including maltose, galactose, lactose, mannose, xylose and ribose (Dokter et al. 1986 a; Oubrie A., Biochim. Biophys. Acta 1647 (2003) 143-151). The reactivity towards sugars other than glucose may in certain cases impair the accuracy of determining blood glucose levels. In particular patients on peritoneal dialysis, treated with icodextrin (a glucose polymer) may contain in their body fluids, e.g., in blood, high levels of other sugars, especially of maltose (Wens, R., et al., Perit. Dial. Int. 18 (1998) 603-609).

Therefore clinical samples as e.g. obtained from diabetic patients, especially from patients with renal complications and especially from patients under dialysis may contain significant levels of other sugars, especially maltose. Glucose determinations in samples obtained from such critical patients may be impaired by maltose (Frampton, J. E. and Plosker, G. L., Drugs 63 (2003) 2079-2105).

There are few reports in the literature on attempts to produce modified PQQ-dependent s-GDHs with altered substrate specificity. Igarashi, S., et al., Biochem. Biophys. Res. Commun. 264 (11999) 820-824 report that introducing a point mutation at position Glu277 leads to mutants with altered substrate specificity profile.

Sode, EP 1 176 202, reports that certain amino acid substitutions within s-GDH lead to mutant s-GDH with an improved affinity for glucose. In EP 1 167 519 the same author reports on mutant s-GDH with improved stability. Furthermore the same author reports in JP2004173538 on other s-GDH mutants with improved affinity for glucose.

Kratzsch, P. et al., WO 02/34919 report that the specificity of s-GDH for glucose as compared to other sugar substrates, especially as compared to maltose, can be improved by amino acid substitutions in certain positions of s-GDH. Central and crucial is a substitution at amino acid position 348. A mutant s-GDH comprising for example a glycine in position 348 instead of a threonine as present in the wild-type s-GDH has a tremendously improved selectivity for the substrate glucose as, e.g. as compared to the substrate maltose. They also disclose that a double mutant having substitutions at positions 348 and 428 have an even more improved specificity for glucose.

In WO 2006/008132 it is shown that an amino acid insertion between amino acids 428 and 429 of s-GDH, especially in combination with an appropriate amino acid substitution at position 348 has quite favorable effects on substrate specificity. Mutants comprising this insertion are for example more specific for the substrate glucose as compared to the substrate maltose.

However, whereas quite some improvements on glucose specificity have been reported, it appears that such improvements frequently and unfortunately go hand in hand with disadvantages like e.g. a reduced stability, a reduced activity and/or a reduced affinity for glucose of such mutated s-GDH. For example, it has become evident that the improved specificity of an s-GDH mutant comprising an amino acid substitution in position 348 goes to the expense of stability, affinity and activity of said mutant as compared to the wild-type enzyme.

A great demand and clinical need therefore exists for further improved mutant forms of s-GDH having a high specificity for glucose and which feature at the same time a reasonable thermo stability, as well as improvements in specific activity or affinity for glucose, or that feature improvements in both specific activity and affinity for glucose.

It was the task of the present invention to provide new mutants or variants of s-GDH with significantly improve thermo stability, specific activity and affinity for glucose as compared to a mutant with improved specificity comprising a substitution at position 348.

It has been found that it is possible to significantly improve the thermo stability, the specific activity and the affinity for glucose of an s-GDH mutant having a substitution at position 348 by selecting mutations from the positions as given in the appending claims.

Due to the improved properties of the new forms of s-GDH, significant technical progress for glucose determinations in various fields of applications is possible. The improved s-GDH mutants according to this invention can for example be used with great advantage for the specific detection or measurement of glucose in biological samples.

SUMMARY

The present invention relates to mutants of s-GDH. A mutant of PQQ-dependent soluble glucose dehydrogenase (s-GDH; EC 1.1.5.2) is disclosed with improved specificity for glucose as compared to maltose, having a substitution of threonine at position 348 by either glycine, alanine or serine and wherein said mutant additionally comprises at least one mutation for improving the stability of the mutant, at least one mutation for improving the affinity of the mutant to glucose, and optionally one or more mutation(s) for further improving the specificity of the mutant for glucose as compared to maltose, and wherein the positions given correspond to the amino acid positions known from the A. calcoaceticus s-GDH wild-type sequence (SEQ ID NO: 2)

Also disclosed are an isolated polynucleotide encoding an s-GDH mutant protein, an expression vector comprising said isolated polynucleotide operably linked to a promoter sequence capable of promoting the expression of said polynucleotide in a host cell and a host cell comprising said expression vector.

Further a process for producing s-GDH mutants comprising culturing the host cell transfected with an appropriate expression vector under conditions suitable for production of an s-GDH mutant is described.

Further disclosed is a method of detecting, determining or measuring glucose in a sample using an improved s-GDH mutant according to the present invention, said improvement comprising contacting the sample with said mutant.

Also described is a device for the detection or measurement of glucose in a sample comprising an improved s-GDH mutant according to the present invention and other reagents required for said measurement.

BRIEF DESCRIPTION OF THE DRAWINGS

The following detailed description of the embodiments of the present invention can be best understood when read in conjunction with the following drawings, where like structure is indicated with like reference numerals and in which:

FIG. 1 shows protein sequences of A. calcoaceticus PQQ-dependent s-GDH (top; SEQ ID NO: 2) and A. baumannii s-GDH (bottom; SEQ ID NO: 22) aligned according to sequence homology.

FIG. 3 shows a nucleotide (DNA) sequence (SEQ ID NO: 3) of the pACSGDH vector referred to in Example 1 containing the wild-type DNA sequence of soluble PQQ-dependent glucose dehydrogenase.

Figure 2:
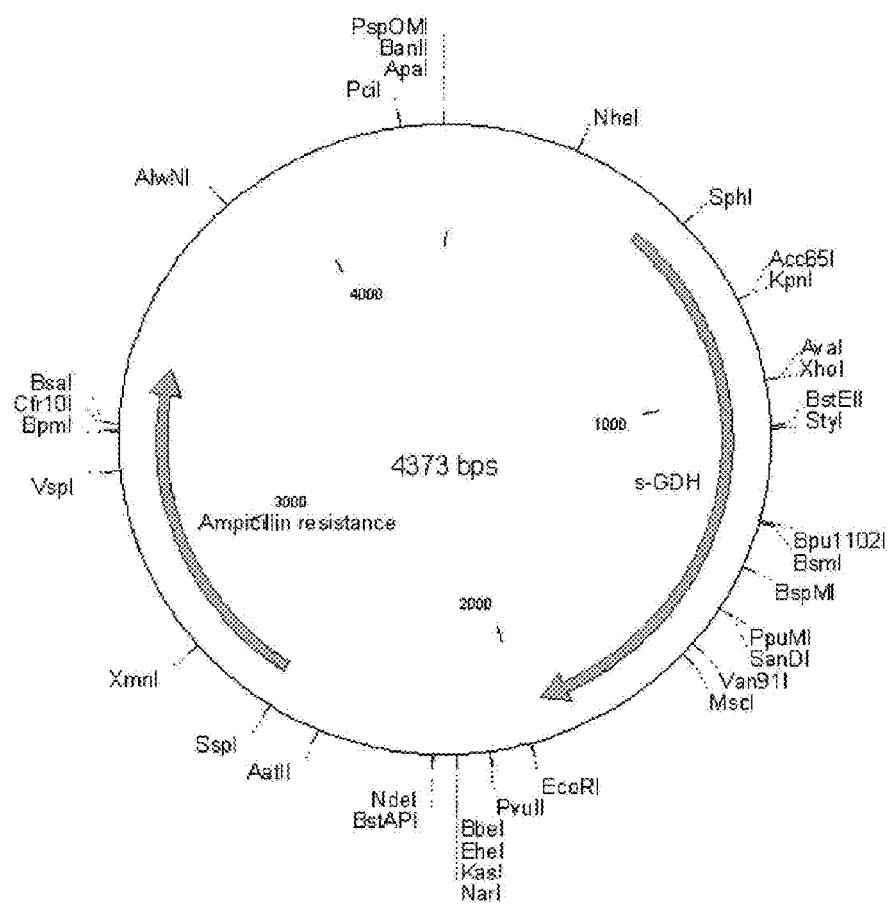
FIG. 2 shows an illustration of pACSGDH vector referred to in Example 1 containing the wild-type or mutated DNA sequences, respectively, of soluble PQQ-dependent glucose dehydrogenase.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

In a first embodiment the invention relates to a mutant of PQQ-dependent soluble glucose dehydrogenase (s-GDH; EC 1.1.5.2) with improved specificity for glucose as compared to maltose, having a substitution of threonine at position 348 by either glycine, alanine or serine and wherein said mutant comprises at least one mutation for improving the stability of the mutant and additionally comprises at least one mutation for improving the affinity of the mutant to glucose, and optionally one or more mutation(s) for further improving the specificity of the mutant for glucose as compared to maltose, and wherein the positions given correspond to the amino acid positions known from the A. calcoaceticus s-GDH wild-type sequence (SEQ ID NO: 2)

As described in WO 02/34919, a substitution of the amino acid in position 348 of the s-GDH sequence corresponding to the wild-type sequence isolated from A. calcoaceticus, can be used to significantly improve the glucose specificity of s-GDH. This is why the improvements described in the framework of the present invention are all described and based on an s-GDH mutant comprising an amino acid substitution at position 348. Preferably the residue threonine at position 348 is substituted with an amino acid residue selected from the group consisting of alanine, glycine, and serine. In a further preferred embodiment glycine or serine is used to substitute for threonine at position 348. The terminology T348G is known to the skilled artisan and indicates that threonine at position 348 is replaced by glycine.

As discussed herein above, two completely different quinoprotein enzyme types with glucose dehydrogenase activity (membrane bound and soluble) are grouped together under EC 1.1.5.2. These two types appear not be related to each other.

For the purpose of this invention only the soluble form of GDH (s-GDH) is relevant and improved mutants thereof are discussed herein below.

It is known in the art that the wild-type DNA-sequence of a soluble PQQ-dependent glucose dehydrogenase can be isolated from strains of Acinetobacter. Most preferred is the isolation of s-GDH from the Acinetobacter calcoaceticus-type strain LMD 79.41. The polypeptide sequence of this wild-type s-GDH (the mature protein) is given in SEQ ID NO; 2 and the DNA sequence is given in SEQ ID NO: 1, respectively. Other LMD strains of Acinetobacter may also be used as source of wild-type s-GDH. Such sequences can be aligned to the sequence obtained from A. calcoaceticus and sequence comparisons be made. It also appears feasible to screen DNA-libraries of other bacterial strains, as for example described for E. coli K-12 (Oubrie, A., et al., J. Mol. Biol. 289 (1999) 319-333) and to identify sequences related to s-GDH in such genomes. Such sequences and yet unidentified, homologous sequences may be used to generate s-GDH mutants with improved thermo stability.

The achievements of the present invention are described in great detail by making reference to amino acid positions known from SEQ ID NO: 2, the wild-type sequence of s-GDH as isolated from Acinetobacter calcoaceticus-type strain LMD 79.41. Amino acid positions in different s-GDH isolates corresponding to positions of SEQ ID NO: 2 are easily identified by appropriate sequence comparison.

The multiple alignment and comparison of an s-GDH sequence with the wild-type sequence of SEQ ID NO: 2 preferably is performed with the PileUp program of GCG Package Version 10.2 (Genetics Computer Group, Inc.). PileUp creates a multiple sequence alignment using a simplification of the progressive alignment method of Feng, D. F. and Doolittle, R. F., J. Mol. Evol. 25 (1987) 351-360, and the scoring matrixes for identical, similar, or different amino acid residues are defined accordingly. This process begins with the pair wise alignment of the two most similar sequences, producing a cluster of two aligned sequences. This cluster can then be aligned to the next most related sequence or cluster of aligned sequences. Two clusters of sequences can be aligned by a simple extension of the pair wise alignment of two individual sequences. The final alignment is achieved by a series of progressive, pair wise alignments that include increasingly dissimilar sequences and clusters, until all sequences have been included in the final pair wise alignment. This way amino acid positions in other, homologous s-GDH molecules can be easily identified as corresponding to the positions given for *A. calcoaceticus* s-GDH in SEQ ID NO: 2. This is why the amino acid positions given herein shall be understood as amino acid positions of SEQ ID NO: 2 or as the positions corresponding thereto in another, homologous s-GDH molecule.

The term "mutant" or "variant" in the sense of the present invention relates to an s-GDH protein which compared to the wild-type amino acid sequence given in SEQ ID NO: 2 exhibits at least one amino acid substitution, deletion or insertion.

The s-GDH mutant may comprise other substitutions and/or deletions and/or insertions provided that an s-GDH mutant of the invention does not differ by more than 45 amino acids from the s-GDH of SEQ ID NO: 2, e.g. that it exhibits at most 45 amino acid substitutions, insertions or deletions in total.

The term "a mutation for improving the stability" refers to any amino substitutions and/or deletions and/or insertions improving the thermo stability of an s-GDH mutant in a short term temperature stress model.

As mentioned above, improvements in glucose specificity appear to be possible only and largely at the expense of a reduced stability, a reduced affinity to glucose or a reduced specific activity or to any combinations of these disadvantageous properties.

Stability according to the present invention is assessed in such a short term stress model and the s-GDH stability as determined in this model is referred to as thermo stability. Thermo stability is determined by measuring the unstressed and stressed s-GDH enzyme activity of a sample. By setting the unstressed sample activity to 100% the remaining activity after stress treatment can be calculated in percent. For mutants of s-GDH with improved substrate specificity, stressing conditions of 64° C. for 30 minutes were chosen. Using these conditions the wild-type enzyme has about 80% of its original activity left, whereas most of the mutants with improved specificity for glucose have only 10% or less of their initial enzymatic activity left after subjecting them to this short-term stress model.

Preferably the mutation for improving the stability of an s-GDH variant having a substitution of threonine at position 348 by either glycine, alanine or serine is a substitution. Preferably said substitution is selected from the group consisting of D87R; N122K; S124K; S146A or G; L187F or M; N267Y; V298L; T313D and L386F.

Also preferred said substitution for improving the stability of an s-GDH variant is selected from the group consisting of D87R; N122K; S124K; S146G; V298L and L386F. In further preferred embodiments combinations of two, three or of four these substitutions or also preferred of all these five substitutions are used in a mutated s-GDH to improve the stability of such mutant.

In a preferred embodiment the s-GDH mutant according to the present invention comprises an arginine in position 87 as known from *A. calcoaceticus* wild-type s-GDH (SEQ ID NO: 2) or in a position corresponding to said position 87 in a homologous enzyme.

In a further preferred embodiment the s-GDH mutant according to the present invention comprises a lysine in position 122 as known from *A. calcoaceticus* wild-type s-GDH (SEQ ID NO; 2) or in a position corresponding to said position 122 in a homologous enzyme.

In a further preferred embodiment the s-GDH mutant according to the present invention comprises a lysine in position 124 as known from *A. calcoaceticus* wild-type s-GDH (SEQ ID NO: 2) or in a position corresponding to said position 124 in a homologous enzyme.

In a further preferred embodiment the s-GDH mutant according to the present invention comprises glycine in position 146 as known from *A. calcoaceticus* wild-type s-GDH (SEQ ID NO: 2) or in a position corresponding to said position 146 in a homologous enzyme.

In a further preferred embodiment the s-GDH mutant according to the present invention comprises leucine in position 298 as known from *A. calcoaceticus* wild-type s-GDH (SEQ ID NO: 2) or in a position corresponding to said position 298 in a homologous enzyme.

In a further preferred embodiment the s-GDH mutant according to the present invention comprises phenylalanine in position 386 as known from *A. calcoaceticus* wild-type s-GDH (SEQ ID NO: 2) or in a position corresponding to said position 386 in a homologous enzyme.

It has been found that six positions of s-GDH appear to be rather important for achieving significant improvements in terms of thermo stability, i.e., positions 87, 122, 124, 146, 298 and 386. What is of significant relevance here is the fact that it has been found that these substitutions have a pronounced effect on the thermo stability of mutants which previously had been generated in order to improve glucose specificity, but at the expense of a reduced thermo stability. In a preferred embodiment the s-GDH mutant according to the present invention comprises a an arginine in position 87, a lysine in position 122 and 124, a glycine in position 146, a leucine in position 298 and a phenylalanine in position 386 of SEQ ID NO:2, or in a position corresponding to said positions if a homologous s-GDH is used.

In a further preferred embodiment the present invention relates to a mutant of PQQ-dependent soluble glucose dehydrogenase (s-GDH; EC 1.1.5.2) with improved specificity for glucose as compared to maltose, having a substitution of threonine at position 348 either by glycine, or by alanine or by serine, wherein said mutant additionally comprises at least one mutation for improving the stability of the mutant and at least one mutation for improving the affinity for glucose of the mutant.

The term "affinity" for a substrate is well known in the art. It is given in mM as the so-called Km-value. Various methods are known to the art to determine the affinity of s-GDH, using glucose or other sugars as substrates, cf., Igarashi, S., et al., Biochem Biophys Res Commun 264 (1999) 820.

In the screening of new variants with crude *E. coli* extract a percentage calculation of the Km-value was performed for faster evaluation of clones generated. The affinity towards glucose for candidate s-GDH mutants was calculated according to the well-known Michaelis-Menten-kinetics.

The s-GDH mutant according to the present invention has an improved affinity for glucose as compared to a mutant comprising a substitution of threonine at position 348 by either glycine, alanine or serine. Preferably the affinity for the substrate glucose is determined as described in detail in the examples section.

Preferably the one or more mutation for improving the affinity for glucose of an s-GDH mutant already comprising a substitution of threonine at position 348 by either glycine, alanine or serine is an amino acid substitution selected from the group consisting of L110H or Y; N229A, G or S; Q246H, M or N; Y333A; G339T; M341V; V349A or G and V436P.

In case the amino acid corresponding to position 110 of the s-GDH wild-type sequence known from *A. calcoaceticus* (SEQ ID NO: 2) is substituted in a variant of the present invention, it is preferred that the naturally occurring amino acid leucine is substituted by an amino acid selected from the group consisting of histidine and tyrosine. More preferred the substitution in position 110 is by histidine.

In case the amino acid corresponding to position 229 of the s-GDH wild-type sequence known from *A. calcoaceticus* (SEQ ID NO: 2) is substituted in a variant of the present invention, it is preferred that the naturally occurring amino acid asparagine is substituted by an amino acid selected from the group consisting of alanine, glycine and serine. More preferred the substitution in position 229 is by alanine.

In case the amino acid corresponding to position 349 of the s-GDH wild-type sequence known from *A. calcoaceticus* (SEQ ID NO. 2) is substituted in a variant of the present invention, it is preferred that the naturally occurring amino acid valine is substituted by an amino acid selected from the group consisting of alanine and glycine. More preferred the substitution in position 349 is by glycine.

Also preferred, the mutation for improving the affinity for glucose is selected from the group consisting of L110H, Q246H; G339T; M341V, V349G and V436P.

Also preferred said substitution for improving the affinity for glucose is selected from Q246H; G339T; M341V and V349G. A preferred s-GDH according to the present invention comprises two or three of these substitutions or all these four substitutions.

In a further preferred embodiment the above described s-GDH mutant with improved specificity for glucose as compared to maltose, having a substitution of threonine at position 348 by either glycine, alanine or serine and comprising at least one mutation for improving the stability additionally comprises one or more mutation(s) for improving the substrate specificity of the mutant to glucose as compared to maltose.

For certain applications the substrate specificity of an s-GDH mutant with improved specificity for glucose as compared to maltose, having a substitution of threonine at position 348 by either glycine, alanine or serine may not yet be sufficient for certain routine applications.

In certain embodiments it may be required to generate an s-GDH mutant that in addition to the above discussed mutation at position 348 comprises one or more additional mutation(s) for further improving the specificity of the mutant for glucose as compared to maltose.

The term "substrate specificity" or "specificity" is well-known to the skilled artisan.

In order to calculate the substrate specificity or cross-reactivity one easy way is to set the activity measured with glucose as substrate to 100% and to compare the activity measured with the other selected sugar to the glucose value. Sometimes, in order not to be redundant, simply the term specificity is used without making special reference to glucose on the one hand and a selected other sugar substrate on the other hand.

The expert in the field will appreciate that comparison of enzymatic activities is best made at equimolar concentrations of the substrate molecules investigated using well-defined assay conditions. Otherwise corrections for differences in concentrations have to be made.

Standardized and well-defined assay conditions have to be chosen in order to assess (improvements in) substrate specificity. The enzymatic activity of s-GDH for glucose as a substrate as well as for other selected sugar substrates is measured as described in the Examples section.

Based on the measurements of enzymatic activity for glucose or for maltose, respectively, cross-reactivity (and improvement thereof) is assessed.

The s-GDH (cross-) reactivity for maltose in percent is calculated as $$\text{Cross-reactivity}[\%] = (\text{activity maltose/activity glucose}) \times 100\%.$$

(Cross-) reactivity for maltose of wild-type s-GDH according to the above formula has been determined as about 105% (see WO 02/34919).

Specificity is calculated according to the following formula:

$$\text{specificity} = \frac{\text{activity glucose mutant}}{\text{activity maltose mutant}} \times \frac{\text{activity maltose wild-type}}{\text{activity glucose wild-type}}$$

Improvements in specificity of a novel s-GDH mutant are recognized as smaller values in the above calculation, as compared to an s-GDH mutant with improved specificity for glucose as compared to maltose, having a substitution of threonine at position 348 by either glycine, alanine or serine.

As the skilled artisan will appreciate the absolute numbers will depend on the number and kind of mutations already present in a mutant. The number and kind of mutations already present in a mutant may be termed the mutant back-ground. Any novel mutation is best compared directly to the mutant back-ground.

Preferably the mutation for further improving the substrate specificity for glucose as compared to maltose is an amino acid substitution selected from the group consisting of Q145P; D163G or N. Q164F; L169F; Y171G; I208L or V; T224I; E245D; G276S; A294D or E; V300A, S, N, Y or I; T307G; T323V; A354Y, E or L; R378I, M, A or D; N428P and insertion 429 P. The term "insertion 429" is used to indicate that between position 428 and position 429 of SEQ ID NO:2 a proline is inserted.

In case the amino acid corresponding to position 169 of the s-GDH wild-type sequence known from *A. calcoaceticus* (SEQ ID NO: 2) is substituted in a variant of the present invention, it is preferred that the naturally occurring amino acid leucine is substituted by phenylalanine, tyrosine or tryptophane. More preferred the substitution in position 169 is by phenylalanine.

In case the amino acid corresponding to position 171 of the s-GDH wild-type sequence known from *A. calcoaceticus* (SEQ ID NO: 2) is substituted in a variant of the present invention, it is preferred that the naturally occurring amino acid tyrosine is substituted by an amino acid selected from the group consisting of from the group consisting of alanine, methionine, glycine. More preferred the substitution in position 171 is by glycine.

In case the amino acid corresponding to position 245 of the s-GDH wild-type sequence known from *A. calcoaceticus* (SEQ ID NO: 2) is substituted in a variant of the present invention, it is preferred that the naturally occurring amino acid glutamic acid is substituted by aspartic acid, asparagine or glutamine. More preferred the substitution in position 245 is by aspartic acid.

In case the amino acid corresponding to position 341 of the s-GDH wild-type sequence known from *A. calcoaceticus* (SEQ ID NO: 2) is substituted in a variant of the present invention, it is preferred that the naturally occurring amino acid methionine is substituted by valine, alanine, leucine or isoleucine. More preferred the substitution in position 341 is by valine.

It has been also found that it is possible to further improve substrate specificity of an s-GDH variant already comprising a substitution at position 348 by insertion of an amino acid, preferably a proline, between position 428 and 429.

Also preferred, the additional mutation for improving the substrate specificity for glucose as compared to maltose is selected from the group consisting of L169F; Y171G; E245D; N428P and insertion 429P.

Preferably, the additional mutation for improving the substrate specificity for glucose as compared to maltose is selected from the group consisting of L169F; Y171G; E245D; and N428P. In further preferred embodiments combinations of two, three or all these four substitutions are used to improve the substrate specificity for glucose as compared to maltose of such mutant. Also preferred, the additional mutation for improving the substrate specificity for glucose as compared to maltose is selected from the group consisting of L169F; Y171 G; E245D; and insertion 429P. In further preferred embodiments combinations of two or of all three substitutions are used together with the insertion 429 P in a mutated s-GDH to improve the substrate specificity for glucose as compared to maltose of such mutant.

As described in WO 02/34919 and WO 2006/008132, respectively, a substitution at position 428 whereby asparagine is replaced by proline or an insertion of the amino acid proline between position 428 and 429, respectively, further improve the specificity of an s-GDH mutant already comprising a substitution at position 348. In a further preferred embodiment the present invention therefore relates to a mutant of PQQ-dependent soluble glucose dehydrogenase (s-GDH; EC 1.1.5.2) with improved specificity for glucose as compared to maltose, having a substitution of threonine at position 348 by either by glycine, by alanine or by serine and either a substitution at position 428 whereby asparagine is replaced by proline or an insertion of the amino acid proline between position 428 and 429, wherein said mutant additionally comprises at least one mutation for improving the stability of the mutant, at least one mutation for improving the specific activity of the mutant, and optionally one or more mutation(s) for improving the affinity of the mutant to glucose, and/or one or more mutation(s) for further improving the specificity of the mutant for glucose as compared to maltose, and wherein the positions given correspond to the amino acid positions known from the *A. calcoaceticus* s-GDH wild-type sequence (SEQ ID NO: 2)

In another embodiment the present invention relates to a mutant of PQQ-dependent soluble glucose dehydrogenase (s-GDH; EC 1.1.5.2) with improved specificity for glucose as compared to maltose, having a substitution of threonine at position 348 by either glycine, alanine or serine, wherein said mutant additionally comprises at least one mutation for improving the stability of the mutant and at least one mutation for improving the specific activity of the mutant.

The term "specific activity" is well-known from the art. It is used to describe the enzymatic activity per amount of protein. Various methods are known to the art to determine specific activity of an s-GDH, using glucose or other sugars as substrates, sc for example Igarashi, S., et al., Biochem Biophys Res Commun 264 (1999) 820. The s-GDH mutant according to the present invention has an improved specific activity for the substrate glucose as compared to a mutant comprising a substitution of threonine at position 348 by either glycine, alanine or serine.

Preferably the mutation for improving the specific activity for glucose is an amino acid substitution selected from the group consisting of H30F or R; A301G or S and A302S or T.

As the skilled artisan will appreciate, it is possible to undertake amino acid substitutions, e.g. silent mutations, which do not influence the properties of s-GDH to a significant extend. The variant according to the present invention will, however, have no more than 45 amino acid exchanges as compared to SEQ ID NO:2. Preferably, the variant will comprise 20 or less amino acid substitutions, more preferred, only 15 amino acid substitutions or fewer substitutions will be present.

Some specific s-GDH variants according to the present invention are given in the Examples section. Preferred s-GDH variants with low glucose interference and improved characteristics regarding thermo stability and substrate affinity for glucose comprise the mutants with the following substitutions:

N122K+L169F+Y171G+E245D+M341V+T348G+ ins429P;

N122K+S124K+L169F+Y171G+E245D+M341V+ T348G+ins429P;

N122K+S124K+L169F+Y171G+E245D+M341V+ T348G+L386F+ins429P;

N122K+S124K+L169F+Y171G+E245D+Q246H+ M341V+T348G+L386F+ins429P;

D87R+N122K+S124K+S146G+L169F+Y171G+ E245D+Q246H+V298L+

M341V+T348S+L386F+ins429P;

D87R+N122K+S124K+S146G+L169F+Y171G+ E245D+Q246H+V298L+

+G339T+M341V+T348G+L386F+ins429P;

D87R+N122K+S124K+S146G+L169F+Y171G+ E245D+Q246H+V298L+

M341V+T348S+L386F+ins429P+V436P;

D87R+N122K+S124K+S146G+L169F+Y171G+ E245D+Q246H+V298L+

M341V+T348S+V349G+A354T+L386F+ins429P;

D87R+L110H+N122K+S124K+S146G+L169F+ Y171G+E245D+Q246H+V298L+M341V+ T348S+L386F+ins429P.

Numerous possibilities are known in the art to produce mutant proteins. Based on the important findings of the present invention disclosing the critical importance of certain residues to improve the thermo stability, the affinity for glucose and the substrate specificity of a mutant s-GDH the skilled artisan now can easily produce Further appropriate variants of s-GDH harboring these and other favorable modifications. Such variants for example can be obtained by the methods known as random mutagenesis (Leung, D. W., et al., Technique 1 (1989) 11-15) and/or site directed mutagenesis (Hill, D. E., et al., Methods Enzymol. 155 (1987) 558-568). An alternative method to produce a protein with the desired properties is to provide chimaeric constructs, which contain sequence elements from at least two different sources or to completely synthesize an appropriate s-GDH gene. Such procedures known in the art may be used in combination with the information disclosed in the present invention to provide mutants or variants of s-GDH comprising e.g. additional amino acid substitutions in combination with the known critical importance of a substitution in position 348 of SEQ ID NO: 2.

An s-GDH variant according to the present invention can e.g., be produced by starting from an s-GDH gene as isolated from Acinetobacter calcoaceticus-type strain LMD 79.41 as well as by starting from a homologous sequence. In the context of this application the term "homologous" is meant to comprise an s-GDH amino acid sequence with at least 90% identity as compared to SEQ ID NO: 2. With other words, after appropriate alignment using the PileUp program, at least 90% of the amino acids of such homologous s-GDH are identical to the amino acids described in SEQ ID NO: 2.

It will be understood that variations of DNA and amino acid sequences naturally exist, or may be intentionally introduced using methods known in the art. These variations may result in up to 10% amino acid differences in the overall sequence, due to deletions, substitutions, insertions, inversions or additions of one or more amino acid residues in said sequence as compared to SEQ ID NO: 2. Such amino acid substitutions may be made, for example, on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine, glycine, alanine, asparagine, glutamine, serine, threonine, phenylalanine, and tyrosine. Other contemplated variations include salts and esters of the afore mentioned polypeptides, as well as precursors of the aforementioned polypeptides, for example, precursors having an N-terminal substitution such as methionine, N-formylmethionine used as leader sequences. Such variations may be made without necessarily departing from the scope and the spirit of the present invention.

According to procedures known in the state of the art or according to the procedures given in the examples section, it is possible to obtain polynucleotide sequences coding for any of the s-GDH mutants as discussed above. The invention therefore comprises also isolated polynucleotide sequences encoding s-GDH mutant proteins according to the present invention as described above.

The present invention further includes an expression vector comprising a nucleic acid sequence according to the present invention operably linked a promoter sequence capable of directing its expression in a host cell.

The present invention further includes an expression vector comprising a nucleic acid sequence according to the present invention operably linked to a promoter sequence capable of directing its expression in a host cell. Preferred vectors are plasmids such as PACSGDH shown in FIGS. 2 and 3.

Expression vectors useful in the present invention typically contain an origin of replication, an antibiotic resistance for selection, a promoter for expression and the whole or part of the s-GDH gene variant. The expression vectors may also include other DNA sequences known in the art, like signal sequences (for a better folding, transportation into the periplasma or secretion), inducers for a better modulation of the expression, or cleavage sites for cloning.

The characteristics of the selected expression vector must be compatible to the host cell, which is to be employed. For example, when cloning in an E. coli cell system, the expression vector should contain promoters isolated from the genome of E. coli cells (e.g., lac, or trp). Suitable origins of replication like the ColE1 plasmid replication origin can be used. Suitable promoters include, for example, lac and trp. It is also preferred that the expression vector includes a sequence coding for a selection marker like an antibiotic resistance gene. As selectable markers, ampicillin resistance, or canamycin resistance may be conveniently employed. All of these materials are known in the art and are commercially available.

Suitable expression vectors containing the desired coding and control sequences may be constructed using standard recombinant DNA techniques known in the art, many of which are described in Sambrook et al., in "Molecular Cloning: A Laboratory Manual" (1989) Cold Spring Harbor, N.Y., Cold Spring Harbor Laboratory Press.

The present invention additionally relates to host cells containing an expression vector which comprises a DNA sequence coding for all or part of the mutant s-GDH. The host cells preferably contain an expression vector that comprises all or part of one of the DNA sequences coding for a mutant s-GDH having one or more mutations shown in the Examples 2-8. Suitable host cells include, for example, E. coli HB101 (ATCC 33694) available from Promega (2800 Woods Hollow Road, Madison, Wis., USA), XL1-Blue MRF' available from Stratagene (11011 North Torrey Pine Road, La Jolla, Calif., USA) and the like.

Expression vectors may be introduced into host cells by various methods known in the art. For example, transformation of host cells with expression vectors can be carried out by polyethylene glycol mediated protoplast transformation method (Sambrook et al. 1989, supra). However, other methods for introducing expression vectors into host cells, for example, electroporation, bolistic injection, or protoplast fusion, can also be employed.

Once an expression vector containing an s-GDH variant has been introduced into an appropriate host cell, the host cell may be cultured under conditions permitting expression of the desired s-GDH variants. Host cells containing the desired expression vector with the DNA sequence coding for all or part of the mutant s-GDH can be easily identified by i.e. antibiotica selection. The expression of the s-GDH variants can be identified by different methods like measuring production of s-GDH mRNA transcripts, detection of the gene product immunologically or detection of the enzymatic activity of the gene product. Preferably an enzymatic assay is applied.

The present invention also teaches the generation and screening of s-GDH mutants. Random mutagenesis and saturation mutagenesis is performed as known in the art. Variants are screened for thermo stability (activity without heat stress treatment compared to remaining activity after heat stress treatment). The assay conditions chosen are adapted to ensure that the expected small enhancements brought about e.g., by a single amino acid substitution, can be measured. One preferred mode of selection or screening of appropriate mutants is given in Example 3. Any change or improvement as compared to the starting enzyme (mutant or wild-type) can be clearly detected.

It should, of course, be understood that not all expression vectors and DNA regulatory sequences would function equally well to express the DNA sequences of the present invention. Neither will all host cells function equally well with the same expression system. However, one of ordinary skill in the art will make an appropriate selection among the expression vectors, DNA regulatory sequences, and host cells using the guidance provided herein without undue experimentation.

The invention also relates to a process for producing s-GDH variants of the current invention comprising culturing a host cell of the invention under conditions suitable for production of the mutant s-GDH of the invention. For bacterial host cells, typical culture conditions are liquid medium containing carbon and nitrogen sources, the appropriate antibiotic and induction agent (depending on the used expression vector). Typical appropriate antibiotics include ampicillin, canamycin, chloroamphenicol, tetracycline and the like. Typical induction agents include IPTG, glucose, lactose and the like.

It is preferred that the polypeptides of the present invention are obtained by production in host cells expressing a DNA sequence coding the mutant s-GDH. The polypeptides of the present invention may also be obtained by in vitro translation of the mRNA encoded by a DNA sequence coding for the mutant s-GDH. For example, the DNA sequences may be synthesized as described above and inserted into a suitable expression vector, which in turn may be used in an in vitro transcription/translation system.

An expression vector comprising an isolated polynucleotide as defined and described above operably linked to a promoter sequence capable of promoting its expression in a cell-free peptide synthesis system represents another preferred embodiment of the present invention.

The polypeptides produced e.g. by procedures as describe above, may then be isolated and purified using various routine protein purification techniques. For example, chromatographic procedures such as ion exchange chromatography, gel filtration chromatography and affinity chromatography may be employed.

One of the major applications of the improved s-GDH variants of this invention is for the use in test strips to monitor the blood-glucose level in diabetic patients. The insensitivity of PQQ-dependent glucose dehydrogenase towards oxygen is, as discussed above, a big advantage over glucose oxidase. The interference due to e.g., maltose, galactose, and/or other related sugars which may be present in a sample to be analyzed, can now be significantly reduced using the novel s-GDH variants having both improved thermo stability as well as improved specificity towards glucose. Of course many kinds of samples may be investigated. Bodily fluids like serum, plasma, intestinal fluid or urine are preferred sources for such samples.

The invention also comprises a method of detecting, determining or measuring glucose in a sample using an s-GDH mutant according to the present invention. It is especially preferred that the improved method for detection of glucose in a sample is characterized in that said detection, determination or measurement of glucose is performed using a sensor or test strip device.

Also within the scope of the present invention is a device for the detection or measurement of glucose in a sample comprising an s-GDH mutant according to this invention as well as other reagents required for said measurement.

The s-GDH variants with improved thermo stability of this invention can also be used to great advantage in biosensors (D'Costa, E. J., et al., Biosensors 2 (1986) 71-87, Laurinavicius, V., et al., Analytical Letters 32 (1999) 299-316; Laurinavicius, V., et al., Monatshefte fuer Chemie 130 (1999) 1269-1281; Woosuck, S. et al., Sensors and Actuators B 100 (2004) 395-402) for online monitoring of glucose in a sample or a reactor. For this purpose, the s-GDH variants can, for example, be used to coat an oxygen-insensitive glassy electrode with an osmium complex containing a redox conductive epoxy network (Ye et al., 1993 supra) for more accurate determination of the glucose concentration.

In the following examples, all reagents, restriction enzymes, and other materials were obtained from Roche Diagnostics Germany, unless other commercial sources are specified, and used according to the instructions given by the suppliers. Operations and methods employed for the purification, characterization and cloning of DNA are well known in the art (Ausubel, F., et al., in "Current protocols in molecular biology" (1994) Wiley Verlag) and can be adapted as required by the skilled artisan.

The following examples further illustrate the present invention. These examples are not intended to limit the scope of the present invention, but provide further understanding of the invention.

The following examples, sequence listing and figures are provided to aid the understanding of the present invention, the true scope of which is set forth in the appended claims. It is understood that modifications can be made in the procedures set forth without departing from the spirit of the invention.

Example 1

Cloning and Expression of the Wild-Type *A. calcoaceticus* Soluble PQQ-Dependent Glucose Dehydrogenase in *E. coli*

The s-GDH gene was isolated from *Acinetobacter calcoaceticus* strain LMD 79.41 according to standard procedures. The wild-type s-GDH gene was subcloned into a plasmid containing the mgl promoter for adjustable expression (cf. Patent application WO 88/09373). The new construct was called pACSGDH (see FIGS. 2 and 3 as well as SEQ ID NO: 3). The recombinant plasmids were introduced into a host organism selected from the *E. coli* group. These organisms were then cultivated under appropriate conditions and colonies showing s-GDH activity selected.

The plasmid pACSGDH was isolated from a 200 ml overnight culture of the clone mentioned above using the QIAGEN Plasmid Maxi Kit (Qiagen) according to the manufacturers' protocol. The plasmid was resuspended in 1 ml bi-distilled water. The concentration of the plasmid was determined using a Beckman DU 7400 Photometer.

The yield was 600 µg. Then the quality of the plasmid was determined by agarose gel electrophoresis.

Example 2

Generating Mutant T348G and Mutant T348S

As starting templates for the generation of further improved variants mutated s-GDH with the mutations T348G or T348S, respectively, was manufactured. These mutants of s-GDH were chosen because they are known to have improved substrate specificity for glucose as compared to the substrate maltose (see WO 02/34919).

The QuickChange Site-Directed Mutagenesis Kit (Stratagene, Cat. 200518) was used to substitute the threonine at position 348 by a glycine or a serine. The appropriate primers were designed.

The 5'- and the 3'-primer used for mutagenesis were complementary to each other and contained the modified codon for the exchange from threonine to glycine (ACA to GGG) or from threonine to serine (ACA to TCA) in a central position. These nucleotides were flanked by 12 to 16 nucleotides at each end. The sequences of the nucleotides were identical to the sense and anti-sense DNA-strand flanking the codon for the amino acid exchange. Instead of the codons ACA=threonine for the sense and TGT for the anti-sense strand, respectively, the primers contained GGG=glycine or TCA=serine, respectively, for the sense and CCC=glycine or AGT=serine, respectively, for the anti-sense strand. The sense and the antisense strand for the exchange T348G are given as SEQ ID NOs: 3 and 4, respectively.

```
CATTTGCTGG CCAGGGGTTG CACCGTCAT   (= SEQ ID NO: 4)

ATGACGGTGC AACCCCTGGC CAGCAAATG   (= SEQ ID NO: 5)
```

The PCR-reaction and the DpnI digestion were performed according to the manual. After that, 1 µl of sample was used for the electroporation of XL-MRF'-cells. Electroporation was achieved with 2.5 KV in 0.2 cm cuvettes using a BioRad E. coli Pulser (BioRad). After growth in 1 ml LB at 37° C. for one hour, bacteria were plated on "4×yeast" medium (20 g yeast extract+5 g NaCl, pH 7.0 to 1 l Aqua dest.)-Ampicillin agar plates (100 µg/ml Ampicillin) and grown over night at 37° C. The mutated s-GDH clones were examined using the following screening method.

Example 3

Screening

The mutant colonies on the agar plates described above where picked into microtiter plates (MTPs) containing 200 µl "4×yeast"-Ampicillin-medium per well and incubated over night at 37° C. These plates are called master plates.

From each master plate, 5 µl sample/well was transferred to an MTP containing 5 µl per well of B (B=Bacterial Protein Extraction Reagent; Pierce No. 78248) for cell disruption and 240 µl of 0.0556 mM pyrolloquinoline quinone (PQQ); 50 mM Hepes; 15 mM CaCl$_2$ pH 7.0/well for activation of s-GDH were added. To complete the formation of the holoenzyme, the MTP was incubated at 25° C. for 2 hours and at 10° C. over night. This plate is called working plate.

From the working plate 4×10 µl sample per well were transferred to four empty MTPs. Thereafter, the first aliquot was tested with glucose at standard concentration (i.e. 30 mM), the second one with a reduced glucose concentration (1.9 mM instead of 30 mM), the third one with maltose as a substrate and the fourth stressed 30 min at 64° C. before testing that aliquot alike the first aliquot. All selected other sugar molecules were used in equimolar standard concentration, i.e. at 30 mM. For all assays 90 µl of mediator solution (see Example 8) already containing the sugar to be analyzed was applied.

The dE/min was calculated and the value using 30 mM glucose as substrate was set to 100% activity. The value obtained with the other sugar was compared to the glucose value and calculated in percent activity ((e.g. for maltose as: dE/min maltose/dE glucose)*100). This is equivalent to the cross-reactivity of the (variant) enzyme. In the following Tables "M/G", i.e. the cross-reactivity of s-GDH with maltose (M) as substrate as compared to glucose (G) as substrate is given.

The value obtained with the 1.9 mM glucose was compared to the 30 mM glucose value and calculated in percent relative activity ((dE/min 1.9 mM glucose/30 mM glucose)*100). This gives a %-value which is an indirect indicator of the Km-value for the variant analyzed. According to this calculation a higher %-value indicates a lower (=better) Km-value.

TABLE 1

Basic characteristics of the mutants T348G and T348S as compared to wild-type (WT) s-GDH

| Enzyme | M/G at 30 mM sugar in % | % relative activity 1.9 mM/ 30 mM glucose | Stability, 30 min, 64° C. | Amino acid (AA) exchange |
|---|---|---|---|---|
| WT | 105% | 70% | 80% | — |
| Mutant A | 22% | 25% | 40% | T348G |
| Mutant A' | 50% | 35% | 50% | T348S |

Example 4

Sequencing of a Mutant s-GDH

The method is exemplified for s-GDH T348G. The sequencing detailed below can also be used for sequencing of other s-GDH mutants.

The following primers were used for sequencing of an s-GDH mutant:

```
                                    (= SEQ ID NO: 6)
Sense strand:     5'-TTA ACG TGC TGA ACA GCC GG-3'

(= SEQ ID NO: 7)
Anti-sense strand: 5'-ATA TGG GTA AAG TAC TAC GC-3'
```

The plasmids containing the gene for mutant s-GDH T348G, which mutant has about 22% maltose/glucose cross-reactivity and s-GDH T348S, which mutant has 50% maltose/glucose cross-reactivity, respectively, were isolated (High Pure Plasmid Isolation Kit, Roche Diagnostics GmbH, No. 1754785) and sequenced using an ABI Prism Dye Terminator Sequencing Kit and ABI 3/73 and 3/77 sequencer (Amersham Pharmacia Biotech).

Sequencing confirmed that the desired mutations on DNA and on amino acid level have been achieved for both mutants. This did result in an exchange from T to G or to S, respectively, at position 348. No additional mutation on the two genes has been found.

Example 5

Further s-GDH Mutants Obtained by Saturation Mutagenesis on the Basis of T348G (Mutant A) and T348S (Mutant A')

Candidate amino acid positions were known to the inventors from previous studies conducted by them. These candidate amino acid positions were suspected or known to influence relevant characteristics of s-GDH like thermo stability, substrate specificity or affinity to glucose were analyzed individually on basis of either T348G (mutant A) or on basis of T348S (mutant A').

Saturation mutagenesis was performed for single amino acid positions in order to evaluate which effect such single amino acid substitution might have on the mutant T348G or T348S, respectively.

The QuickChange Site-Directed Mutagenesis Kit (Stratagene, Cat. 200518) was used to substitute successively wild type amino acids at positions 87, 110, 122, 124, 145, 146, 169, 171, 187, 246, 294, 298, 300, 313, 323, 333, 339, 341, 349, 378, 428, and 436 of the wild-type s-GDH-protein, respectively.

The 5'- and the 3'-primer used for mutagenesis were chosen to be complementary to each other and contained NNN (N=A, C, G or T) in a central position. The three randomly incorporated nucleotides N, which are at the desired position and coding for the amino acid position under investigation were flanked by 12 to 16 nucleotides at each end which were identical to the sense and antisense DNA-strand of the template. Instead of the wild-type codon, the primers contained NNN therefore the oligonucleotides coded for every possible codon.

For each of the positions under investigation, one PCR reaction was performed.

The PCR-reactions and the DpnI-restriction endonuclease digestions were performed according to the manual provided with the QuickChange Site-Directed Mutagenesis Kit (Stratagene, Cat. 200518).

From each PCR reaction 1 µl was used for the electroporation of XL1F-cells. Cells were grown and the s-GDH-activities of the clones were determined as described above.

To increase the statistical likelihood that all 20 possible amino acids substitutions are covered in this evaluation, 200 clones for each position were screened as described in Example 3. Interesting clones were sequenced according to the method given in Example 4.

TABLE 2

Effect of additional amino acid substitutions on basic characteristics of mutant A (=T348G)

| Enzyme | M/G at 30 mM sugar in % | % relative activity 1.9 mM/ 30 mM glucose | Stability, 30 min, 64° C. | Amino acid (AA) exchange |
|---|---|---|---|---|
| Wt-GlucDOR | 105% | 70% | 80% | — |
| Mutant A | 22% | 25% | 40% | T348G |
| Mutant A/1 | — | 30% | — | +L110H |
| Mutant A/2 | — | 28% | — | +L110Y |
| Mutant A/3 | 40% | 50% | — | +Q246H |
| Mutant A/4 | 33% | 30% | — | +Q246M |
| Mutant A/5 | 35% | 33% | — | +Q246N |
| Mutant A/6 | — | 30% | — | +Y333A |
| Mutant A/7 | 55% | 40% | — | +G339T |
| Mutant A/8 | 30% | 45% | — | +V436P |
| Mutant A/9 | 28% | 30% | — | +M341V |
| Mutant A/10 | 25% | 28% | 40% | +V349A |
| Mutant A/11 | 26% | 28% | 40% | +V349G |
| Mutant A/12 | 20% | 27% | — | +Q145P |
| Mutant A/13 | 17% | 30% | — | +A294D |
| Mutant A/14 | 15% | 30% | — | +A294E |
| Mutant A/15 | 20% | 28% | — | +V300A |
| Mutant A/16 | 20% | 28% | — | +V300S |
| Mutant A/17 | 20% | 28% | — | +V300N |
| Mutant A/18 | 20% | 28% | — | +V300Y |
| Mutant A/19 | 20% | 28% | — | +V300I |
| Mutant A/20 | 17% | 25% | — | +T323V |
| Mutant A/21 | 18% | 26% | — | +R378I |
| Mutant A/22 | 19% | 26% | — | +R378M |
| Mutant A/23 | 17% | 26% | — | +R378A |
| Mutant A/24 | 17% | 28% | — | +R378D |
| Mutant A/25 | 15% | 22% | — | +E245D |
| Mutant A/26 | 18% | 32% | 30% | +L169F |
| Mutant A/27 | 18% | 31% | 28% | +Y171G |
| Mutant A/28 | 12% | 20% | 20% | +Ins429P |
| Mutant A/29 | — | — | 50% | +D87R |
| Mutant A/30 | — | — | 70% | +S146A |
| Mutant A/31 | — | — | 75% | +S146G |
| Mutant A/32 | — | — | 45% | +L187F |
| Mutant A/33 | — | — | 50% | +N122K |
| Mutant A/34 | — | — | 45% | +S124K |
| Mutant B | 10% | 35% | 50% | T348G + N428P |

TABLE 3

Effect of additional amino acid substitutions on basic characteristics of mutant A' (=T348S)

| Enzyme | M/G at 30 mM sugar in % | % relative activity 1.9 mM/ 30 mM glucose | Stability, 30 min, 64° C. | Amino acid (AA) exchange |
|---|---|---|---|---|
| Wt-GlucDOR | 105% | 70% | 80% | — |
| Mutant A' | 50% | 35% | 50% | T348S |
| Mutant A'/1 | 55% | 47% | — | +L110H |
| Mutant A'/2 | 65% | 70% | — | +Q246H |
| Mutant A'/3 | 58% | 50% | — | +Q246M |
| Mutant A'/4 | 60% | 55% | — | +Q246N |
| Mutant A'/5 | 59% | 50% | — | +G339T |
| Mutant A'/6 | 60% | 60% | — | +V436P |
| Mutant A'/7 | 40% | 35% | — | +A294D |
| Mutant A'/8 | 38% | 32% | — | +A294E |
| Mutant A'/9 | 41% | 45% | — | +T323V |
| Mutant A'/10 | 43% | 47% | — | +R378I |
| Mutant A'/11 | 44% | 47% | — | +R378M |
| Mutant A'/12 | 40% | 50% | — | +R378A |
| Mutant A'/13 | 40% | 50% | — | +R378D |
| Mutant A'/14 | — | — | 60% | +D87R |
| Mutant A'/15 | — | — | 80% | +S146A |
| Mutant A'/16 | — | — | 85% | +S146G |
| Mutant A'/17 | — | — | 65% | +V298L |
| Mutant A'/18 | — | — | 60% | +T313D |
| Mutant A'/19 | — | — | 75% | +L386F |

Amino acid exchanges with a positive effect on substrate specificity, affinity for glucose and/or thermo stability of mutant A or mutant A', respectively can be derived from Tables 2 and 3.

Example 6

Identification of Mutants with Improved Thermo Stability

Experiments have been expanded to mutants having rather good substrate specificity for glucose as compared to maltose, but at the cost of disadvantages like too low thermo stability or a too low affinity for glucose.

So-called mutant 6 has a quite favorable low cross-reactivity to maltose that is only about 1.5% of the reactivity as measured for glucose. Mutant 6 is characterized by the amino acid substitutions Y171G, E245D, M341V and T348G and it has an insertion of a proline (ins429P) between positions 428 and 429.

The following primers were used to introduce these desired amino acid substitutions:

```
                                          (SEQ ID NO: 8)
Sense     5'-CCTATAAGAAAAAGACAGATACGCTCG-3'
strand
                                          (SEQ ID NO: 9)
Antisense 5'-CGAGCGTATCTGTCTTTTTCTTATAGG-3'
strand D87R:
                                         (SEQ ID NO: 10)
Sense     5'-TTCCATCCTCGAGAGATTGTCAAT-3'
strand
                                         (SEQ ID NO: 11)
Antisense 5'-ATTGACAATCTCTCTGAGGATGGAA-3'
strand N122K and S124K:
                                         (SEQ ID NO: 12)
Sense     5'-CGTTATACCTATAAGAAAAAGACAGATACGCTCG-3'
strand
                                         (SEQ ID NO: 13)
Antisense 5'-CGAGCGTATCTGTCTTTTTCTTATAGGTATAACG-3'
strand S146G:
                                         (SEQ ID NO: 14)
Sense     5'-AAAAGACCATCAGGGTGGTCTCGAGAAG-3'
strand
                                         (SEQ ID: NO: 15)
Antisense 5'-CTTCTCGAGACCACCCTGATGGTCTTTT-3'
strand V298L:
                                         (SEQ ID NO: 16)
Sense     5'-GCTCAAAATGGATTAAAAGTAGCCGCA-3'
strand
                                         (SEQ ID: NO: 17)
Antisense 5'-TGCGGCTACTTTATTTCCATTTTGAGC-3'
strand L386F:
                                         (SEQ ID NO: 18)
Sense     5'-CCGTATTAAGTTCGATCCAACTTATAGC-3'
strand
                                         (SEQ ID NO: 19)
Antisense 5'-GCTATAAGTTGGATCGAACTTAATACGG-3'
strand
```

TABLE 4

Mutations with positive impact on thermo stability of s-GDH mutants already comprising other mutants for e.g. improving glucose specificity

| Enzyme | % M/G at 30 mM sugar in | Stability, 30 min, 64° C. | Amino acid exchanges |
|---|---|---|---|
| WT | 105% | 80% | — |
| Mutant A | 25% | 40% | T348G |
| Mutant V | 25% | 50% | T348G + T313D |
| Mutant VI | 25% | 45% | T348G + N267Y |
| Mutant 6 | 1.5% | 5% | N122K + L169F + Y171G + E245D + M341V + T348G + ins429P |
| Mutant 19 | 2% | 10% | N122K + S124K + L169F + Y171G + E245D + M341V + T348G + ins429P |
| Mutant 21 | 2% | 15% | N122K + S124K + L169F + Y171G + E245D + M341V + T348G + L386F + ins429P |
| Mutant 24 | 2% | 25% | N122K + S124K + L169F + Y171G + E245D + M341V + T348G + L386F + ins429P |
| Mutant 22 | 2.5% | 20% | N122K + S124K + L169F + Y171G + E245D + Q246H + M341V + T348G + L386F + ins429P |
| Mutant 25 | 2.5% | 55% | N122K + S124K + L169F + Y171G + E245D + Q246H + M341V + T348G + L386F + ins429P |
| Mutant 29 | 2.5% | 75% | D87R + N122K + S124K + S146G + L169F + Y171G + E245D + Q246H + V298L + M341V + T348S + L386F + ins429P |
| Mutant 30 | 2.5% | 60% | D87R + N122K + S124K + S146G + L169F + Y171G + E245D + Q246H + V298L ++ G339T + M341V + T348G + L386F + ins429P |

TABLE 4-continued

Mutations with positive impact on thermo stability of s-GDH mutants already comprising other mutants for e.g. improving glucose specificity

| Enzyme | % M/G at 30 mM sugar in | Stability, 30 min, 64° C. | Amino acid exchanges |
|---|---|---|---|
| Mutant 31 | 3% | 80% | D87R + N122K + S124K + S146G + L169F + Y171G + E245D + Q246H + V298L + M341V + T348S + L386F + ins429P + V436P |
| Mutant 32 | 3.3% | 67% | D87R + N122K + S124K + S146G + L169F + Y171G + E245D + Q246H + V298L + M341V + T348S + V349G + A354T + L386F + ins429P |
| Mutant 33 | 4.3% | 80% | D87R + L110H + N122K + S124K + S146G + L169F + Y171G + E245D + Q246H + V298L + M341V + T348S + L386F + ins429P |

The above results show that the amino acid exchanges D87R, N122K, S124K, S146A or G, preferably G, S146G, L187F or M; N267Y, V298L, T313D and L386F improve the thermo stability of the basic mutant 6.

The substitution D87R; N122K; S124K; S146G; V298L and L386F have quite strong effects on improvements in thermo stability.

Example 7

Generating Mutants with High Substrate Specificity for Glucose as Compared to Maltose and Improvement of Affinity Towards Glucose In WO 02/34919 several amino acid exchanges at different positions of s-GDH have been identified and shown to enhance the substrate specificity for glucose as compared to e.g., maltose. Combinations of the amino acid exchange T348G with amino acid substitutions at other positions for example at positions 169, 171, 245, 341 and/or 349 enhanced the substrate specificity furthermore. Several different s-GDH mutants with improved specificity for glucose but as compared to maltose but with rather a low affinity for the substrate glucose were selected and attempts made to improve their affinity for glucose.

As is known from the experiments summarized in Tables 2 and 3 the amino acid substitutions L110H or Y; N229A, G or S; Q246H, M or N; Y333A; G339T; M341V; V349A or G and V436P appear appropriate to enhance the affinity of an s-GDH mutant for glucose. Strongest effects on affinity are seen with the mutants L110H, Q246H; G339T; M341V; V349G and V436P. Further strong improvements of affinity were found with the amino acid exchanges Q246H, M341V; V349G and V436P. Point mutations are introduced into already existing mutants by the same strategy as already exemplified in Example 6, therefore here only the specific primers for the substitutions Q246H are given.

```
                          (SEQ ID NO: 20)
Sense stand    5'-GGTAAATTATTGCAGTCTGATCATGGCCC-3'

(SEQ ID: NO: 21)
Antisense      5'-GGGCCATGATCAGACTGCAATAATTTACC-3'
strand
```

The determination of affinity to glucose via the screening Km-value measurement as described in Example 3 was performed. The apparent Km-value was calculated from the plots of different substrate concentration versus enzyme activity.

The specific activity was worked out as described in Example 8.

Combinations of exchanges identified as appropriate for improving substrate specificity, affinity and/or stability have been introduced into mutated s-GDH with starkly improved specificity for glucose as compared to maltose.

TABLE 5

Combination of various amino acid substitutions in s-GDH mutants with improved substrate specificity for glucose as compared to maltose

| Enzymes | screening Km-value in % | app. Km-value mM Glucose | app. Km-value mM Maltose | M/G in % | Specific activity U/mg |
|---|---|---|---|---|---|
| WT | 70 | 0.7 | 1.4 | 105 | 800 |
| Mutant 6 | 8 | 64.7 | 714 | 1.5 | 268 |
| Mut. 13 (=Mutant 6 + Q246H) | 20 | 17.1 | 208 | 3 | 430 |
| Mutant G | 12 | 11 | 110 | 2 | 351 |
| Mut. J (=Mutant G + Q246H) | 18 | 8 | 143 | 3 | 489 |
| Mutant 22 | 18 | 11 | n.d. | 2.5 | 400 |
| Mutant 23 (=mutant 22, + Q246N) | 15 | 13 | n.d. | 2 | 350 |
| Mutant 29 (like mutant 22, but T348S) | 21 | 11 | n.d. | 2.5 | 400 |
| Mutant 30 (=mutant 22 + G339T) | 26 | 9 | n.d. | 2.5 | 350 |
| Mutant 31 (=mutant 29 + V436P) | 33 | 6 | n.d. | 3 | 380 |
| Mutant 32 (=mutant 29 + V349G + A354T) | 32 | n.d. | n.d. | 3.3 | 220 |
| Mutant 33 (=mutant 29 + L110H) | 28 | n.d. | n.d. | 4.3 | 350 |

It can be clearly seen that on all mutant types the additional amino acid exchange Q246H produced an enhancement of affinity towards glucose and an improvement concerning specific activity. Mutant 6 has the amino acid exchanges at position T348G, N122K, L169F, Y171G, E245D, M341V and an insertion of proline at position 429 as mutant 13 and additional Q246H. Mutant J has the amino acid exchanges at position T348G, Y171G, E245D, M341V, N428P as mutant 0 and additional Q246H.

Mutant 22 has the amino acid exchanges at position T348G, N122K, S124K, L169F, Y171G, E245D, Q246H, M341V, L386F and an insertion of proline at position 429. Mutant 29 has all the exchanges of mutant 22 except T348G, which is exchanged to T348S, and resulted in an improvement of velocity. Mutant 30 and 31 achieved even higher Km-values for glucose by exchanging additionally G339T and V436P.

Example 8

Purification of Wild-Type or Variant s-GDH and Analysis of Enzymatic Activity and Specific Activity, Respectively

*E. coli* cells comprising an appropriate s-GDH expression vector are grown (4×yeast-Amp. 37° C.), harvested and resuspended in potassium phosphate buffer pH 7.0. Cell disruption was performed by French Press passage (700-900 bar). After centrifugation the supernatant was applied to a S-Sepharose (Amersham Pharmacia Biotec) column equilibrated with 10 mM potassium phosphate buffer pH 7.0. After washing, the s-GDH was eluted using a salt gradient 0-1 M NaCl. The fractions showing s-GDH activity were pooled, dialyzed against potassium phosphate buffer pH 7.0 and re-chromatographed on re-equilibrated S-sepharose column. The active fractions were pooled and subjected to a gel filtration using a Superdex® 200 column (Amersham). The active fractions were pooled and after addition of $CaCl_2$ (3 mM end concentration) stored at −20° C.

Protein determination was performed using the Protein Assay Reagent no. 23225 from Pierce (calibration curve with BSA, 30 Min. 37° C.).

For measurement of the enzyme activity the s-GDH samples were diluted to 1 mg protein/ml with 0.0556 mM pyrroloquinoline quinone (PQQ); 50 mM Hepes; 15 mM $CaCl_2$ pH 7.0 and incubated at 25° C. for 30 minutes for reconstitution or activation.

After activation, samples were diluted with 50 mM Hepes; 15 mM $CaCl_2$ pH 7.0 to approximately 0.02 U/ml, and 50 µl of each diluted sample was added to 1000 µl of a 0.2 M citrate buffer solution (pH 5.8; at 25° C.) containing 0.315 mg (4-(dimethylphosphinylmethyl)-2-methyl-pyrazolo-[1.5a]-imidazol-3-yl)-(4-nitro-sophenyl)-amine (see U.S. Pat. No. 5,484,708)/ml as a mediator and 30 mM sugar.

Extinction at 620 nm is monitored during the first 5 minutes at 25° C.

One Unit enzyme activity corresponds to the conversion of 1 mMol mediator/min under the above assay conditions Calculation:

$$\text{Volume Activity (U/ml)} = (\text{total volume} * dE/\min[U/ml]):(\epsilon * \text{sample volume} * 1)$$

($\epsilon$=coefficient of extinction; $\epsilon_{620\,nm}$=30[1*mmol$^{-1}$*cm$^{-1}$]).

Specific Activity (U/mg)=Volume activity U/ml divided by protein concentration mg/ml results in U/mg The assays were performed with glucose and maltose (Merck, Germany), respectively.

Results relating to enzyme activity as well as to specific activity have been included into the Tables given in the previous Examples.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. An isolated mutant of PQQ-dependent soluble glucose dehydrogenase (s-GDH) that relative to the *A. calcoaceticus* s-GDH wild-type polypeptide of SEQ ID NO: 2 has improved specificity for glucose as compared to maltose, said mutant comprising an s-GDH polypeptide, said s-GDH polypeptide consisting of an amino acid sequence having at least 90% sequence identity with the *A. calcoaceticus* s-GDH wild-type sequence of SEQ ID NO: 2, wherein said mutant differs from SEQ ID NO: 2 by a substitution at position 348 of either glycine, alanine or serine; and
   a) at least one stabilizing mutation selected from the group consisting of D87R; N122K; S124K; S146G; V298L and L386F;
   b) at least one glucose affinity mutation selected from the group consisting of L110H L110Y; N229A, N229G, N229S, Q246H, Q246M, Q246N, Y333A; G339T, M341V, V349A, V349G and V436P, and optionally;
   c) one or more glucose specificity mutation(s) selected from the group consisting of Q145P, D163G, D163N, A164F, L169F, Y171G, I208L, I208V, T224I, E245D, G276S, A294D, A294E; V300A, V300S, V300N, V300Y, V300I, T307G, T323V, A354Y, A354E, A354L, R378I, R378M, R378A, R378D, N428P and insertion 429 P; and wherein the mutant has s-GDH activity and the designated positions correspond to the amino acid positions known from the *A. calcoaceticus* s-GDH wild-type sequence of SEQ ID NO: 2.

2. The s-GDH mutant according to claim 1, wherein said glucose affinity mutation is selected from the group consisting of L110H, Q246H, G339T, M341V, V349G and V436P.

3. An isolated mutant of PQQ-dependent soluble glucose dehydrogenase (s-GDH), said mutant comprising an s-GDH polypeptide, said s-GDH polypeptide consisting of an amino acid sequence having at least 90% sequence identity with the *A. calcoaceticus* s-GDH wild-type sequence of SEQ ID NO: 2, wherein said mutant differs from SEQ ID NO: 2 by a substitution at position 348 of either glycine, alanine or serine; and a substitution selected from the group consisting of D87R, N122K, S124K, S146G, V298L and L386F, further wherein the mutant has s-GDH activity, and the designated positions correspond to amino acid positions from the *A. calcoaceticus* s-GDH wild-type sequence of SEQ ID NO: 2.

4. The s-GDH mutant according to claim 2, wherein said glucose specificity mutation is selected from the group consisting of L169F, Y171G, E245D, N428P and insertion 429P.

5. A method of detecting, determining or measuring glucose in a sample using a s-GDH mutant according to any of claims 1, 2, 3 or 4, said improvement comprising contacting the sample with said mutant.

6. The method of claim 5 further characterized in that said detection, determination or measurement of glucose is performed using a sensor or test strip device.

7. The s-GDH mutant according to claim 1 wherein said glucose affinity mutation consists of two or three amino acid substitutions relative to the *A. calcoaceticus* s-GDH wild-type sequence of SEQ ID NO: 2, said two or three amino acid substitutions selected from the group consisting of Q246H, G339T, M341V and V349G.

8. The s-GDH mutant according to claim 2 wherein said glucose affinity mutation for improving the affinity to glucose is selected from the group consisting of Q246H, G339T, M341V and V349G.

9. The s-GDH mutant according to claim 1 wherein said glucose affinity mutation is Q246H, and said glucose specificity mutation comprises a mutation selected from the group consisting of L169F, Y171G, E245D, E245D, and insertion 429 P, relative to the *A. calcoaceticus* s-GDH wild-type sequence of SEQ ID NO: 2.

10. An isolated mutant of PQQ-dependent soluble glucose dehydrogenase (s-GDH) that relative to the *A. calcoaceticus* s-GDH wild-type sequence of SEQ ID NO: 2 has improved specificity for glucose as compared to maltose, said mutant comprising an s-GDH polypeptide, wherein said s-GDH polypeptide consists of an amino acid sequence having at least 90% sequence identity with the *A. calcoaceticus* s-GDH wild-type sequence of SEQ ID NO: 2, wherein said mutant differs from SEQ ID NO: 2 by a substitution at position 348 of either glycine, alanine or serine;

an insertion of proline at position 429; and the following amino acid substitutions, T348G, N122K, S124K, L169F, Y171G, E245D, Q246H, M341V and L386F.

11. The s-GDH mutant according to claim 1 wherein said s-GDH polypeptide sequence differs from the *A. calcoaceticus* s-GDH wild-type sequence of SEQ ID NO: 2 by a substitution at position 348 of either glycine, alanine or serine;

an insertion of proline at position 429; and the following amino acid substitutions, T348S, N122K, S124K, L169F, Y171G, E245D, Q246H, M341V and L386F.

12. The s-GDH mutant according to claim 1 wherein said s-GDH polypeptide sequence differs from the *A. calcoaceticus* s-GDH wild-type sequence of SEQ ID NO: 2 by a substitution at position 348 of either glycine, alanine or serine;

an insertion of proline at position 429 and the following amino acid substitutions, T348G, N122K, S124K, L169F, Y171G, E245D, Q246H, M341V, L386F and G339T.

13. The s-GDH mutant according to claim 1 wherein said s-GDH polypeptide sequence differs from the *A. calcoaceticus* s-GDH wild-type sequence of SEQ ID NO: 2 by a substitution at position 348 of either glycine, alanine or serine;

an insertion of proline at position 429; and the following amino acid substitutions, T348G, N122K, S124K, L169F, Y171G, E245D, Q246H, M341V, L386F and V436P.

14. The s-GDH mutant according to claim 1 wherein said stabilizing mutation consists of substitutions N122K, S124K and L386F, said glucose affinity mutation consists of substitutions Q246H and M341V, and said glucose specificity mutation consists of substitutions T348G, L169F, Y171G and E245D.

15. The s-GDH mutant according to claim 14 wherein said mutant only differs from the amino acid sequence of SEQ ID NO: 2 by the amino acid substitutions N122K, S124K and L386F, Q246H and M341V, T348G, L169F, Y171G and E245D.

* * * * *

UNITED STATES PATENT AND TRADEMARK OFFICE
CERTIFICATE OF CORRECTION

PATENT NO. : 7,732,179 B2 Page 1 of 1
APPLICATION NO. : 12/250241
DATED : June 8, 2010
INVENTOR(S) : Boenitz-Dulat et al.

It is certified that error appears in the above-identified patent and that said Letters Patent is hereby corrected as shown below:

In the claims, Claim 1, Column 43, line 55, please delete "A164F" and insert -- Q164F -- therefor.

In Claim 9, Column 45, line 1, please delete the second instance of "E245D.".

Signed and Sealed this

Thirteenth Day of July, 2010

David J. Kappos
*Director of the United States Patent and Trademark Office*

SEQUENCE LISTING

<160> NUMBER OF SEQ ID NOS: 22

<210> SEQ ID NO 1
<211> LENGTH: 1362
<212> TYPE: DNA
<213> ORGANISM: Acinetobacter calcoaceticus
<220> FEATURE:
<221> NAME/KEY: CDS
<222> LOCATION: (1)..(1362)

<400> SEQUENCE: 1

```
gat gtt cct cta act cca tct caa ttt gct aaa gcg aaa tca gag aac      48
Asp Val Pro Leu Thr Pro Ser Gln Phe Ala Lys Ala Lys Ser Glu Asn
1               5                   10                  15 ttt gac aag aaa gtt att cta tct aat cta aat aag ccg cac gcg ttg      96
Phe Asp Lys Lys Val Ile Leu Ser Asn Leu Asn Lys Pro His Ala Leu
                20                  25                  30 tta tgg gga cca gat aat caa att tgg tta act gag cga gca aca ggt     144
```

```
Leu Trp Gly Pro Asp Asn Gln Ile Trp Leu Thr Glu Arg Ala Thr Gly
         35                  40                  45 aag att cta aga gtt aat cca gag tcg ggt agt gta aaa aca gtt ttt      192
Lys Ile Leu Arg Val Asn Pro Glu Ser Gly Ser Val Lys Thr Val Phe
 50                  55                  60 cag gta cca gag att gtc aat gat gct gat ggg cag aat ggt tta tta      240
Gln Val Pro Glu Ile Val Asn Asp Ala Asp Gly Gln Asn Gly Leu Leu
 65                  70                  75                  80 ggt ttt gcc ttc cat cct gat ttt aaa aat aat cct tat atc tat att      288
Gly Phe Ala Phe His Pro Asp Phe Lys Asn Asn Pro Tyr Ile Tyr Ile
                 85                  90                  95 tca ggt aca ttt aaa aat ccg aaa tct aca gat aaa gaa tta ccg aac      336
Ser Gly Thr Phe Lys Asn Pro Lys Ser Thr Asp Lys Glu Leu Pro Asn
                100                 105                 110 caa acg att att cgt cgt tat acc tat aat aaa tca aca gat acg ctc      384
Gln Thr Ile Ile Arg Arg Tyr Thr Tyr Asn Lys Ser Thr Asp Thr Leu
            115                 120                 125 gag aag cca gtc gat tta tta gca gga tta cct tca tca aaa gac cat      432
Glu Lys Pro Val Asp Leu Leu Ala Gly Leu Pro Ser Ser Lys Asp His
130                 135                 140 cag tca ggt cgt ctt gtc att ggg cca gat caa aag att tat tat acg      480
Gln Ser Gly Arg Leu Val Ile Gly Pro Asp Gln Lys Ile Tyr Tyr Thr
145                 150                 155                 160 att ggt gac caa ggg cgt aac cag ctt gct tat ttg ttc ttg cca aat      528
Ile Gly Asp Gln Gly Arg Asn Gln Leu Ala Tyr Leu Phe Leu Pro Asn
                165                 170                 175 caa gca caa cat acg cca act caa caa gaa ctg aat ggt aaa gac tat      576
Gln Ala Gln His Thr Pro Thr Gln Gln Glu Leu Asn Gly Lys Asp Tyr
                180                 185                 190 cac acc tat atg ggt aaa gta cta cgc tta aat ctt gat gga agt att      624
His Thr Tyr Met Gly Lys Val Leu Arg Leu Asn Leu Asp Gly Ser Ile
            195                 200                 205 cca aag gat aat cca agt ttt aac ggg gtg gtt agc cat att tat aca      672
Pro Lys Asp Asn Pro Ser Phe Asn Gly Val Val Ser His Ile Tyr Thr
210                 215                 220 ctt gga cat cgt aat ccg cag ggc tta gca ttc act cca aat ggt aaa      720
Leu Gly His Arg Asn Pro Gln Gly Leu Ala Phe Thr Pro Asn Gly Lys
225                 230                 235                 240 tta ttg cag tct gaa caa ggc cca aac tct gac gat gaa att aac ctc      768
Leu Leu Gln Ser Glu Gln Gly Pro Asn Ser Asp Asp Glu Ile Asn Leu
                245                 250                 255 att gtc aaa ggt ggc aat tat ggt tgg ccg aat gta gca ggt tat aaa      816
Ile Val Lys Gly Gly Asn Tyr Gly Trp Pro Asn Val Ala Gly Tyr Lys
                260                 265                 270 gat gat agt ggc tat gct tat gca aat tat tca gca gca gcc aat aag      864
Asp Asp Ser Gly Tyr Ala Tyr Ala Asn Tyr Ser Ala Ala Ala Asn Lys
            275                 280                 285 tca att aag gat tta gct caa aat gga gta aaa gta gcc gca ggg gtc      912
Ser Ile Lys Asp Leu Ala Gln Asn Gly Val Lys Val Ala Ala Gly Val
290                 295                 300 cct gtg acg aaa gaa tct gaa tgg act ggt aaa aac ttt gtc cca cca      960
Pro Val Thr Lys Glu Ser Glu Trp Thr Gly Lys Asn Phe Val Pro Pro
305                 310                 315                 320 tta aaa act tta tat acc gtt caa gat acc tac aac tat aac gat cca     1008
Leu Lys Thr Leu Tyr Thr Val Gln Asp Thr Tyr Asn Tyr Asn Asp Pro
                325                 330                 335 act tgt gga gag atg acc tac att tgc tgg cca aca gtt gca ccg tca     1056
Thr Cys Gly Glu Met Thr Tyr Ile Cys Trp Pro Thr Val Ala Pro Ser
                340                 345                 350
```

```
tct gcc tat gtc tat aag ggc ggt aaa aaa gca att act ggt tgg gaa   1104
Ser Ala Tyr Val Tyr Lys Gly Gly Lys Lys Ala Ile Thr Gly Trp Glu
        355                 360                 365 aat aca tta ttg gtt cca tct tta aaa cgt ggt gtc att ttc cgt att   1152
Asn Thr Leu Leu Val Pro Ser Leu Lys Arg Gly Val Ile Phe Arg Ile
370                 375                 380 aag tta gat cca act tat agc act act tat gat gac gct gta ccg atg   1200
Lys Leu Asp Pro Thr Tyr Ser Thr Thr Tyr Asp Asp Ala Val Pro Met
385                 390                 395                 400 ttt aag agc aac aac cgt tat cgt gat gtg att gca agt cca gat ggg   1248
Phe Lys Ser Asn Asn Arg Tyr Arg Asp Val Ile Ala Ser Pro Asp Gly
                405                 410                 415 aat gtc tta tat gta tta act gat act gcc gga aat gtc caa aaa gat   1296
Asn Val Leu Tyr Val Leu Thr Asp Thr Ala Gly Asn Val Gln Lys Asp
            420                 425                 430 gat ggc tca gta aca aat aca tta gaa aac cca gga tct ctc att aag   1344
Asp Gly Ser Val Thr Asn Thr Leu Glu Asn Pro Gly Ser Leu Ile Lys
        435                 440                 445 ttc acc tat aag gct aag                                           1362
Phe Thr Tyr Lys Ala Lys
    450

<210> SEQ ID NO 2
<211> LENGTH: 454
<212> TYPE: PRT
<213> ORGANISM: Acinetobacter calcoaceticus

<400> SEQUENCE: 2

Asp Val Pro Leu Thr Pro Ser Gln Phe Ala Lys Ala Lys Ser Glu Asn
1               5                   10                  15

Phe Asp Lys Lys Val Ile Leu Ser Asn Leu Asn Lys Pro His Ala Leu
            20                  25                  30

Leu Trp Gly Pro Asp Asn Gln Ile Trp Leu Thr Glu Arg Ala Thr Gly
        35                  40                  45

Lys Ile Leu Arg Val Asn Pro Glu Ser Gly Ser Val Lys Thr Val Phe
    50                  55                  60

Gln Val Pro Glu Ile Val Asn Asp Ala Asp Gly Gln Asn Gly Leu Leu
65                  70                  75                  80

Gly Phe Ala Phe His Pro Asp Phe Lys Asn Asn Pro Tyr Ile Tyr Ile
                85                  90                  95

Ser Gly Thr Phe Lys Asn Pro Lys Ser Thr Asp Lys Glu Leu Pro Asn
            100                 105                 110

Gln Thr Ile Ile Arg Arg Tyr Thr Tyr Asn Lys Ser Thr Asp Thr Leu
        115                 120                 125

Glu Lys Pro Val Asp Leu Leu Ala Gly Leu Pro Ser Ser Lys Asp His
    130                 135                 140

Gln Ser Gly Arg Leu Val Ile Gly Pro Asp Gln Lys Ile Tyr Tyr Thr
145                 150                 155                 160

Ile Gly Asp Gln Gly Arg Asn Gln Leu Ala Tyr Leu Phe Leu Pro Asn
                165                 170                 175

Gln Ala Gln His Thr Pro Thr Gln Gln Glu Leu Asn Gly Lys Asp Tyr
            180                 185                 190

His Thr Tyr Met Gly Lys Val Leu Arg Leu Asn Leu Asp Gly Ser Ile
        195                 200                 205

Pro Lys Asp Asn Pro Ser Phe Asn Gly Val Val Ser His Ile Tyr Thr
    210                 215                 220

Leu Gly His Arg Asn Pro Gln Gly Leu Ala Phe Thr Pro Asn Gly Lys
```

-continued

```
             225                 230                 235                 240

Leu Leu Gln Ser Glu Gln Gly Pro Asn Ser Asp Asp Glu Ile Asn Leu
                245                 250                 255

Ile Val Lys Gly Gly Asn Tyr Gly Trp Pro Asn Val Ala Gly Tyr Lys
            260                 265                 270

Asp Asp Ser Gly Tyr Ala Tyr Ala Asn Tyr Ser Ala Ala Asn Lys
        275                 280                 285

Ser Ile Lys Asp Leu Ala Gln Asn Gly Val Lys Val Ala Ala Gly Val
    290                 295                 300

Pro Val Thr Lys Glu Ser Glu Trp Thr Gly Lys Asn Phe Val Pro Pro
305                 310                 315                 320

Leu Lys Thr Leu Tyr Thr Val Gln Asp Thr Tyr Asn Tyr Asn Asp Pro
                325                 330                 335

Thr Cys Gly Glu Met Thr Tyr Ile Cys Trp Pro Thr Val Ala Pro Ser
            340                 345                 350

Ser Ala Tyr Val Tyr Lys Gly Gly Lys Lys Ala Ile Thr Gly Trp Glu
        355                 360                 365

Asn Thr Leu Leu Val Pro Ser Leu Lys Arg Gly Val Ile Phe Arg Ile
    370                 375                 380

Lys Leu Asp Pro Thr Tyr Ser Thr Thr Tyr Asp Asp Ala Val Pro Met
385                 390                 395                 400

Phe Lys Ser Asn Asn Arg Tyr Arg Asp Val Ile Ala Ser Pro Asp Gly
                405                 410                 415

Asn Val Leu Tyr Val Leu Thr Asp Thr Ala Gly Asn Val Gln Lys Asp
            420                 425                 430

Asp Gly Ser Val Thr Asn Thr Leu Glu Asn Pro Gly Ser Leu Ile Lys
        435                 440                 445

Phe Thr Tyr Lys Ala Lys
    450

<210> SEQ ID NO 3
<211> LENGTH: 4373
<212> TYPE: DNA
<213> ORGANISM: artificial sequence
<220> FEATURE:
<223> OTHER INFORMATION: Sequence vector pACSGDH

<400> SEQUENCE: 3
cactaactga ttacgcaccg catgtaaccg ttttcaatct gtgagtaaat tcacagttta      60
ttaacattgt gatagctatg atgacaacgt tgtcgcact gtaactaacg tgtaacagtt     120
agttgtcagt tttgctgggg tatttcgctt ataaaaaccg ttatcacaat atcccgcgac    180
taccggacaa aaataaagag ttgaataaga gcttatccca ttagggctat tttacttgcc    240
attttggacc tgggcagtgc tcgccaaaac gcgttagcgt tttgaacgcg ctagcggcgg    300
cccgaagggc gagcgtagcg agtcaaacct cacgtactac gtgtacgctc cggttttgc     360 gcgctgtccg tgtccaaact gctgcgccaa taacgcctgg tgggataggc tctaaatacg    420
cttcggcgtt cagtaacacg cgttaacgtg ctgaacagcc gggcattttt ttacgctata    480
ccctacataa taaaaccgga gctaccatga ataagaaggt actgaccctt tctgccgtga    540 tgcaagtct gttattcggc gcgcacgcg atgccgccga tgttcctcta actccatctc     600
aatttgctaa agcgaaatca gagaactttg acaagaaagt tattctatct aatctaaata    660
agccgcacgc gttgttatgg ggaccagata atcaaatttg ttaactgag cgagcaacag    720 gtaagattct aagagttaat ccagagtcgg gtagtgtaaa aacagttttt caggtaccag    780
```

-continued

```
agattgtcaa tgatgctgat gggcagaatg gtttattagg ttttgccttc catcctgatt    840
ttaaaaataa tccttatatc tatatttcag gtacatttaa aaatccgaaa tctacagata    900
aagaattacc gaaccaaacg attattcgtc gttataccta taataaatca acagatacgc    960
tcgagaagcc agtcgattta ttagcaggat taccttcatc aaaagaccat cagtcaggtc   1020
gtcttgtcat tgggccagat caaaagattt attatacgat tggtgaccaa gggcgtaacc   1080
agcttgctta tttgttcttg ccaaatcaag cacaacatac gccaactcaa caagaactga   1140
atggtaaaga ctatcacacc tatatgggta aagtactacg cttaaatctt gatgaagta    1200
ttccaaagga taatccaagt tttaacgggg tggttagcca tatttataca cttggacatc   1260
gtaatccgca gggcttagca ttcactccaa atggtaaatt attgcagtct gaacaaggcc   1320
caaactctga cgatgaaatt aacctcattg tcaaaggtgg caattatggt tggccgaatg   1380
tagcaggtta taaagatgat agtggctatg cttatgcaaa ttattcagca gcagccaata   1440
agtcaattaa ggatttagct caaaatggag taaaagtagc cgcagggggtc cctgtgacga   1500
aagaatctga atggactggt aaaaactttg tcccaccatt aaaaacttta tataccgttc   1560
aagataccta caactataac gatccaactt gtggagagat gacctacatt tgctggccaa   1620
cagttgcacc gtcatctgcc tatgtctata agggcggtaa aaaagcaatt actggttggg   1680
aaaatacatt attggttcca tctttaaaac gtggtgtcat tttccgtatt aagttagatc   1740
caacttatag cactacttat gatgacgctg taccgatgtt taagagcaac aaccgttatc   1800
gtgatgtgat tgcaagtcca gatgggaatg tcttatatgt attaactgat actgccggaa   1860
atgtccaaaa agatgatggc tcagtaacaa atacattaga aaacccagga tctctcatta   1920
agttcaccta taaggctaag taatacagtc gcattaaaaa accgatctat aaagatcggt   1980
tttttagtt ttagaaaaga attcactggc cgtcgtttta caacgtcgtg actgggaaaa   2040
ccctggcgtt acccaactta atcgccttgc agcacatccc cctttcgcca gctggcgtaa   2100
tagcgaagag gcccgcaccg atcgcccttc ccaacagttg cgcagcctga atggcgaatg   2160
gcgcctgatg cggtattttc tccttacgca tctgtgcggt atttcacacc gcatatggtg   2220
cactctcagt acaatctgct ctgatgccgc atagttaagc cagccccgac acccgccaac   2280
acccgctgac gcgccctgac gggcttgtct gctcccggca tccgcttaca gacaagctgt   2340
gaccgtctcc gggagctgca tgtgtcagag gttttcaccg tcatcaccga aacgcgcgag   2400
acgaaagggc ctcgtgatac gcctattttt ataggttaat gtcatgataa taatggtttc   2460
ttagacgtca ggtggcactt ttcggggaaa tgtgcgcgga acccctattt gtttattttt   2520
ctaaatacat tcaaatatgt atccgctcat gagacaataa ccctgataaa tgcttcaata   2580
atattgaaaa aggaagagta tgagtattca acatttccgt gtcgccctta ttccctttttt   2640
tgcggcattt tgccttcctg tttttgctca cccagaaacg ctggtgaaag taaaagatgc   2700
tgaagatcag ttgggtgcac gagtgggtta catcgaactg gatctcaaca gcggtaagat   2760
ccttgagagt tttcgccccg aagaacgttt tccaatgatg agcactttta aagttctgct   2820
atgtggcgcg gtattatccc gtattgacgc cgggcaagag caactcggtc gccgcataca   2880
ctattctcag aatgacttgg ttgagtactc accagtcaca gaaaagcatc ttacggatgg   2940
catgacagta agagaattat gcagtgctgc cataaccatg agtgataaca ctgcggccaa   3000
cttacttctg acaacgatcg gaggaccgaa ggagctaacc gcttttttgc acaacatggg   3060
ggatcatgta actcgccttg atcgttggga accggagctg aatgaagcca taccaaacga   3120
```

| | |
|---|---|
| cgagcgtgac accacgatgc ctgtagcaat ggcaacaacg ttgcgcaaac tattaactgg | 3180 |
| cgaactactt actctagctt cccggcaaca attaatagac tggatggagg cggataaagt | 3240 |
| tgcaggacca cttctgcgct cggcccttcc ggctggctgg tttattgctg ataaatctgg | 3300 |
| agccggtgag cgtgggtctc gcggtatcat tgcagcactg gggccagatg gtaagccctc | 3360 |
| ccgtatcgta gttatctaca cgacggggag tcaggcaact atggatgaac gaaatagaca | 3420 |
| gatcgctgag ataggtgcct cactgattaa gcattggtaa ctgtcagacc aagtttactc | 3480 |
| atatatactt tagattgatt taaaacttca ttttaattt aaaggatct aggtgaagat | 3540 |
| ccttttgat aatctcatga ccaaaatccc ttaacgtgag ttttcgttcc actgagcgtc | 3600 |
| agacccgta gaaaagatca aaggatcttc ttgagatcct tttttctgc gcgtaatctg | 3660 |
| ctgcttgcaa acaaaaaaac caccgctacc agcggtggtt tgtttgccgg atcaagagct | 3720 |
| accaactctt tttccgaagg taactggctt cagcagagcg cagataccaa atactgtcct | 3780 |
| tctagtgtag ccgtagttag gccaccactt caagaactct gtagcaccgc ctacatacct | 3840 |
| cgctctgcta atcctgttac cagtggctgc tgccagtggc gataagtcgt gtcttaccgg | 3900 |
| gttggactca agacgatagt taccggataa ggcgcagcgg tcgggctgaa cggggggttc | 3960 |
| gtgcacacag cccagcttgg agcgaacgac ctacaccgaa ctgagatacc tacagcgtga | 4020 |
| gctatgagaa agcgccacgc ttcccgaagg agaaaggcg acaggtatc cggtaagcgg | 4080 |
| cagggtcgga acaggagagc gcacgaggga gcttccaggg ggaaacgcct ggtatcttta | 4140 |
| tagtcctgtc gggtttcgcc acctctgact tgagcgtcga ttttgtgat gctcgtcagg | 4200 |
| ggggcggagc ctatggaaaa acgccagcaa cgcggccttt ttacggttcc tggccttttg | 4260 |
| ctggcctttt gctcacatgt tctttcctgc gttatcccct gattctgtgg ataaccgtat | 4320 |
| taccgccttt gagtgagctg ataccgctcg ccgcagccga acgacgggc ccg | 4373 |

```
<210> SEQ ID NO 4
<211> LENGTH: 29
<212> TYPE: DNA
<213> ORGANISM: Artificial sequence
<220> FEATURE:
<223> OTHER INFORMATION: primer

<400> SEQUENCE: 4
```

| | |
|---|---|
| catttgctgg ccagggggttg caccgtcat | 29 |

```
<210> SEQ ID NO 5
<211> LENGTH: 29
<212> TYPE: DNA
<213> ORGANISM: Artificial sequence
<220> FEATURE:
<223> OTHER INFORMATION: primer

<400> SEQUENCE: 5
```

| | |
|---|---|
| atgacggtgc aaccccctggc cagcaaatg | 29 |

```
<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
```

| | |
|---|---|
| ttaacgtgct gaacagccgg | 20 |

```
<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
atatgggtaa agtactacgc                                          20

<210> SEQ ID NO 8
<211> LENGTH: 27
<212> TYPE: DNA
<213> ORGANISM: Artificial Sequence
<220> FEATURE:
<223> OTHER INFORMATION: primer

<400> SEQUENCE: 8
cctataagaa aaagacagat acgctcg                                  27

<210> SEQ ID NO 9
<211> LENGTH: 27
<212> TYPE: DNA
<213> ORGANISM: Artificial Sequence
<220> FEATURE:
<223> OTHER INFORMATION: primer

<400> SEQUENCE: 9
cgagcgtatc tgtcttttc ttatagg                                   27

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
ttccatcctc gagagattgt caat                                     24

<210> SEQ ID NO 11
<211> LENGTH: 25
<212> TYPE: DNA
<213> ORGANISM: Artificial Sequence
<220> FEATURE:
<223> OTHER INFORMATION: primer

<400> SEQUENCE: 11
attgacaatc tctctgagga tggaa                                    25

<210> SEQ ID NO 12
<211> LENGTH: 34
<212> TYPE: DNA
<213> ORGANISM: Artificial Sequence
<220> FEATURE:
<223> OTHER INFORMATION: primer

<400> SEQUENCE: 12
cgttatacct ataagaaaaa gacagatacg ctcg                          34

<210> SEQ ID NO 13
<211> LENGTH: 34
<212> TYPE: DNA
<213> ORGANISM: Artificial Sequence
<220> FEATURE:
<223> OTHER INFORMATION: primer
```

<400> SEQUENCE: 13
cgagcgtatc tgtcttttc ttataggtat aacg                                34

<210> SEQ ID NO 14
<211> LENGTH: 28
<212> TYPE: DNA
<213> ORGANISM: Artificial Sequence
<220> FEATURE:
<223> OTHER INFORMATION: primer

<400> SEQUENCE: 14
aaaagaccat cagggtggtc tcgagaag                                      28

<210> SEQ ID NO 15
<211> LENGTH: 28
<212> TYPE: DNA
<213> ORGANISM: Artificial Sequence
<220> FEATURE:
<223> OTHER INFORMATION: primer

<400> SEQUENCE: 15
cttctcgaga ccaccctgat ggtcttt                                       28

<210> SEQ ID NO 16
<211> LENGTH: 27
<212> TYPE: DNA
<213> ORGANISM: Artificial Sequence
<220> FEATURE:
<223> OTHER INFORMATION: primer

<400> SEQUENCE: 16
gctcaaaatg gattaaaagt agccgca                                       27

<210> SEQ ID NO 17
<211> LENGTH: 27
<212> TYPE: DNA
<213> ORGANISM: Artificial Sequence
<220> FEATURE:
<223> OTHER INFORMATION: primer

<400> SEQUENCE: 17
tgcggctact ttatttccat tttgagc                                       27

<210> SEQ ID NO 18
<211> LENGTH: 28
<212> TYPE: DNA
<213> ORGANISM: Artificial Sequence
<220> FEATURE:
<223> OTHER INFORMATION: primer

<400> SEQUENCE: 18
ccgtattaag ttcgatccaa cttatagc                                      28

<210> SEQ ID NO 19
<211> LENGTH: 28
<212> TYPE: DNA
<213> ORGANISM: Artificial Sequence
<220> FEATURE:
<223> OTHER INFORMATION: primer

<400> SEQUENCE: 19
gctataagtt ggatcgaact taatacgg                                      28

<210> SEQ ID NO 20
<211> LENGTH: 29

<212> TYPE: DNA
<213> ORGANISM: Artificial Sequence
<220> FEATURE:
<223> OTHER INFORMATION: primer

<400> SEQUENCE: 20
ggtaaattat tgcagtctga tcatggccc                                    29

<210> SEQ ID NO 21
<211> LENGTH: 29
<212> TYPE: DNA
<213> ORGANISM: Artificial Sequence
<220> FEATURE:
<223> OTHER INFORMATION: primer

<400> SEQUENCE: 21
gggccatgat cagactgcaa taatttacc                                    29

<210> SEQ ID NO 22
<211> LENGTH: 455
<212> TYPE: PRT
<213> ORGANISM: Acinetobacter baumannii

<400> SEQUENCE: 22

```
Asp Ile Pro Leu Thr Pro Ala Gln Phe Ala Lys Ala Lys Thr Glu Asn
1               5                   10                  15

Phe Asp Lys Lys Val Ile Leu Ser Asn Leu Asn Lys Pro His Ala Leu
            20                  25                  30

Leu Trp Gly Pro Asp Asn Gln Ile Trp Leu Thr Glu Arg Ala Thr Gly
        35                  40                  45

Lys Ile Leu Arg Val Asn Pro Val Ser Gly Ser Ala Lys Thr Val Phe
    50                  55                  60

Gln Val Pro Glu Ile Val Ser Asp Ala Asp Gly Gln Asn Gly Leu Leu
65                  70                  75                  80

Gly Phe Ala Phe His Pro Asp Phe Lys His Asn Pro Tyr Ile Tyr Ile
                85                  90                  95

Ser Gly Thr Phe Lys Asn Pro Lys Ser Thr Asp Lys Glu Leu Pro Asn
            100                 105                 110

Gln Thr Ile Ile Arg Arg Tyr Thr Tyr Asn Lys Thr Thr Asp Thr Phe
        115                 120                 125

Glu Lys Pro Ile Asp Leu Ile Ala Gly Leu Pro Ser Ser Lys Asp His
    130                 135                 140

Gln Ser Gly Arg Leu Val Ile Gly Pro Asp Gln Lys Ile Tyr Tyr Thr
145                 150                 155                 160

Ile Gly Asp Gln Gly Arg Asn Gln Leu Ala Tyr Leu Phe Leu Ser Asn
                165                 170                 175

Gln Ala Gln His Thr Pro Thr Gln Gln Glu Leu Asn Ser Lys Asp Tyr
            180                 185                 190

His Thr Tyr Met Gly Lys Val Leu Arg Leu Asn Leu Asp Gly Ser Ile
        195                 200                 205

Pro Lys Asp Asn Pro Ser Phe Asn Gly Val Val Ser His Ile Tyr Thr
    210                 215                 220

Leu Gly His Arg Asn Pro Gln Gly Leu Ala Phe Ala Pro Asn Gly Lys
225                 230                 235                 240

Leu Leu Gln Ser Glu Gln Gly Pro Asn Ser Asp Asp Glu Ile Asn Leu
                245                 250                 255

Val Leu Lys Gly Gly Asn Tyr Gly Trp Pro Asn Val Ala Gly Tyr Lys
            260                 265                 270
```

```
Asp Asp Ser Gly Tyr Ala Tyr Ala Asn Tyr Ser Ala Ala Thr Asn Lys
        275                 280                 285

Ser Gln Ile Lys Asp Leu Ala Gln Asn Gly Ile Lys Val Ala Thr Gly
        290                 295                 300

Val Pro Val Thr Lys Glu Ser Glu Trp Thr Gly Lys Asn Phe Val Pro
305                     310                 315                 320

Pro Leu Lys Thr Leu Val Thr Val Gln Asp Thr Tyr Asn Tyr Asn Asp
                325                 330                 335

Pro Thr Cys Gly Glu Met Ala Tyr Ile Cys Trp Pro Thr Val Ala Pro
            340                 345                 350

Ser Ser Ala Tyr Val Tyr Thr Gly Gly Lys Lys Ala Ile Pro Gly Trp
        355                 360                 365

Glu Asn Thr Leu Leu Val Pro Ser Leu Lys Arg Gly Val Ile Phe Arg
        370                 375                 380

Ile Lys Leu Asp Pro Thr Tyr Ser Thr Thr Leu Asp Asp Ala Ile Pro
385                     390                 395                 400

Met Phe Lys Ser Asn Asn Arg Tyr Arg Asp Val Ile Ala Ser Pro Glu
                405                 410                 415

Gly Asn Thr Leu Tyr Val Leu Thr Asp Thr Ala Gly Asn Val Gln Lys
            420                 425                 430

Asp Asp Gly Ser Val Thr His Thr Leu Glu Asn Pro Gly Ser Leu Ile
            435                 440                 445

Lys Phe Thr Tyr Asn Gly Lys
        450                 455
```